(12) United States Patent
Perera et al.

(10) Patent No.: US 9,433,501 B2
(45) Date of Patent: Sep. 6, 2016

(54) INFLATION MEDIA FOR IMPLANTS

(75) Inventors: Aruna Perera, Santa Rosa, CA (US);
Trevor Greenan, Santa Rosa, CA (US);
Larry Rogers, San Rafael, CA (US)

(73) Assignee: DIRECT FLOW MEDICAL, INC., Santa Rosa, CA (US)

( * ) Notice: Subject to any disclaimer, the term of this patent is extended or adjusted under 35 U.S.C. 154(b) by 1243 days.

(21) Appl. No.: 13/110,812

(22) Filed: May 18, 2011

(65) Prior Publication Data

US 2012/0022629 A1    Jan. 26, 2012

Related U.S. Application Data

(60) Provisional application No. 61/346,419, filed on May 19, 2010.

(51) Int. Cl.

| | |
|---|---|
| *C08L 63/00* | (2006.01) |
| *C08G 59/50* | (2006.01) |
| *A61F 2/24* | (2006.01) |
| *A61F 2/06* | (2013.01) |
| *A61M 25/00* | (2006.01) |
| *A61M 25/06* | (2006.01) |
| *B29C 47/00* | (2006.01) |
| *B29L 31/00* | (2006.01) |

(52) U.S. Cl.
CPC ............ *A61F 2/2439* (2013.01); *A61F 2/2418* (2013.01); *A61F 2/2436* (2013.01); *C08G 59/5026* (2013.01); *C08L 63/00* (2013.01); *A61F 2210/0085* (2013.01); *A61F 2220/0008* (2013.01); *A61F 2220/0016* (2013.01); *A61F 2250/0003* (2013.01); *A61M 25/005* (2013.01); *A61M 25/0009* (2013.01); *A61M 25/0023* (2013.01); *A61M 25/0054* (2013.01); *A61M 2025/0046* (2013.01); *A61M 2025/0681* (2013.01); *B29C 47/0028* (2013.01); *B29L 2031/7542* (2013.01); *G01N 2203/0071* (2013.01); *G01N 2203/0073* (2013.01)

(58) Field of Classification Search
None
See application file for complete search history.

(56) References Cited

U.S. PATENT DOCUMENTS

| | | | |
|---|---|---|---|
| 3,657,744 | A | 4/1972 | Ersek |
| 3,671,979 | A | 6/1972 | Moulopoulos |
| 4,056,854 | A | 11/1977 | Boretos et al. |
| 4,189,548 | A * | 2/1980 | Sakashita et al. ............ 525/109 |
| 4,900,848 | A * | 2/1990 | Saito et al. ................... 549/517 |
| 5,087,688 | A * | 2/1992 | Gruber et al. ................. 528/99 |
| 5,370,691 | A | 12/1994 | Samson |

(Continued)

FOREIGN PATENT DOCUMENTS

WO    WO 2011/146759    11/2011

OTHER PUBLICATIONS

International Search Report and Written Opinion for Appl. No. PCT/US2011/037222 mailed Feb. 9, 2012.

*Primary Examiner* — Mark Kaucher
*Assistant Examiner* — Kregg Brooks
(74) *Attorney, Agent, or Firm* — Knobbe, Martens, Olson & Bear, LLP

(57) ABSTRACT

An inflatable implant is disclosed. The inflatable implant comprises at least one inflation channel for forming an inflatable structure of the inflatable implant; and an inflation media disposed within the at least one inflation channel, wherein the inflation media comprises a mixture of an epoxy resin and a hardener, the mixture is configured to gel at about 37° C in less than about 2.5 hours after mixing to form a gelled mixture.

14 Claims, 17 Drawing Sheets

(56) References Cited

U.S. PATENT DOCUMENTS

| | | |
|---|---|---|
| 5,411,552 A | 5/1995 | Andersen et al. |
| 5,423,851 A | 6/1995 | Samuels |
| 5,534,024 A | 7/1996 | Rogers et al. |
| 5,554,180 A | 9/1996 | Turk |
| 5,554,185 A | 9/1996 | Block et al. |
| 5,871,537 A | 2/1999 | Holman et al. |
| 5,957,949 A | 9/1999 | Leonhardt et al. |
| 5,980,570 A | 11/1999 | Simpson |
| 6,007,575 A | 12/1999 | Samuels et al. |
| 6,059,823 A | 5/2000 | Holman et al. |
| 6,168,614 B1 | 1/2001 | Andersen et al. |
| 6,280,412 B1 | 8/2001 | Pederson, Jr. et al. |
| 6,395,019 B2 | 5/2002 | Chobotov |
| 6,582,462 B1 | 6/2003 | Andersen et al. |
| 6,761,733 B2 | 7/2004 | Chobotov et al. |
| 7,125,464 B2 | 10/2006 | Chobotov et al. |
| 7,150,758 B2 | 12/2006 | Kari et al. |
| 7,192,441 B2 | 3/2007 | Sherry |
| 7,276,078 B2 | 10/2007 | Spenser et al. |
| 7,320,704 B2 | 1/2008 | Lashinski et al. |
| 7,534,261 B2 | 5/2009 | Friedman |
| 7,615,071 B2 | 11/2009 | Chobotov |
| 7,628,800 B2 | 12/2009 | Sherman et al. |
| 7,666,220 B2 | 2/2010 | Evans et al. |
| 7,678,217 B2 | 3/2010 | Chobotov et al. |
| 7,766,954 B2 | 8/2010 | Chobotov et al. |
| 7,803,178 B2 | 9/2010 | Whirley et al. |
| 8,002,826 B2 | 8/2011 | Seguin |
| 8,012,201 B2 | 9/2011 | Lashinski et al. |
| 8,092,525 B2 | 1/2012 | Eliasen et al. |
| 2002/0024170 A1* | 2/2002 | Takeshima et al. .......... 264/489 |
| 2003/0125797 A1 | 7/2003 | Chobotov et al. |
| 2004/0006341 A1 | 1/2004 | Shaolian et al. |
| 2005/0137701 A1 | 6/2005 | Salahieh et al. |
| 2006/0212112 A1 | 9/2006 | Evans et al. |
| 2006/0222860 A1* | 10/2006 | Basheer et al. ............... 428/414 |
| 2006/0235512 A1 | 10/2006 | Osborne et al. |
| 2006/0271172 A1 | 11/2006 | Tehrani |
| 2008/0039923 A1 | 2/2008 | Taylor et al. |
| 2009/0076605 A1 | 3/2009 | Linares |
| 2009/0318949 A1 | 12/2009 | Ganpath et al. |
| 2009/0319029 A1 | 12/2009 | Evans et al. |
| 2010/0004728 A1 | 1/2010 | Rao et al. |
| 2010/0016942 A1 | 1/2010 | Chobotov et al. |
| 2010/0168844 A1 | 7/2010 | Toomes et al. |
| 2011/0098802 A1 | 4/2011 | Braido et al. |
| 2012/0016468 A1 | 1/2012 | Robin et al. |
| 2012/0022629 A1 | 1/2012 | Perera et al. |

\* cited by examiner

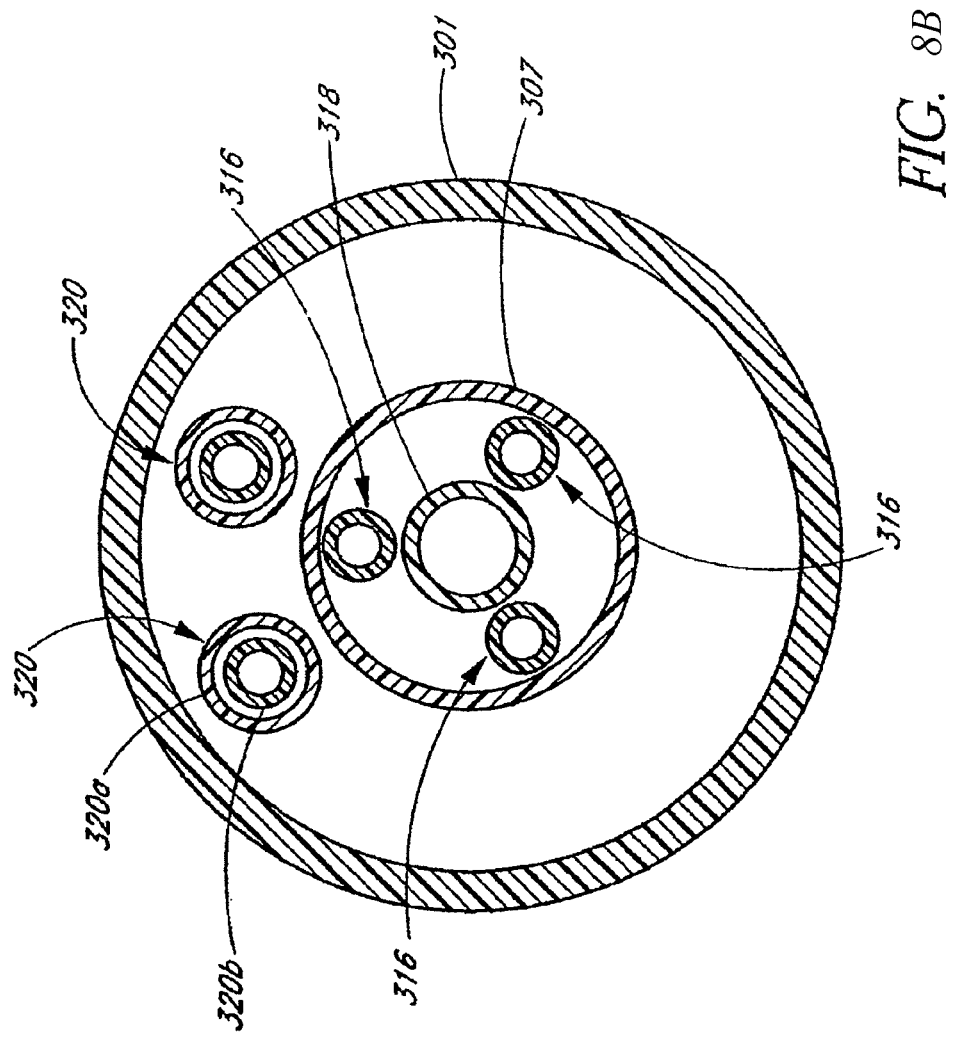

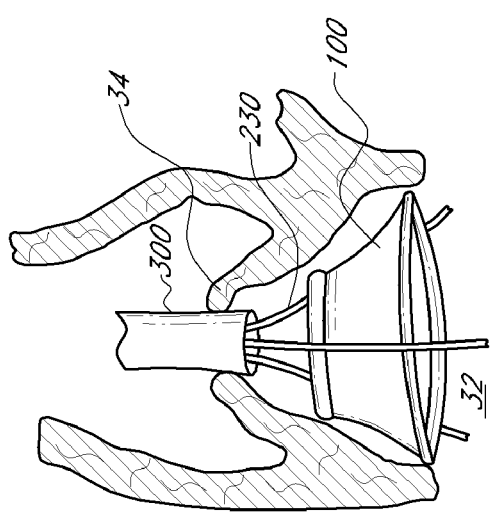
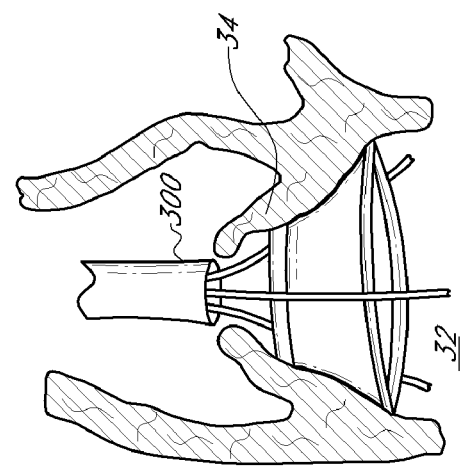
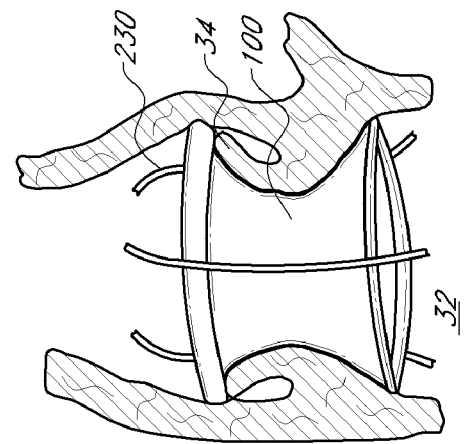
FIG. 10A
FIG. 10B
FIG. 10C

INFLATION MEDIA FOR IMPLANTS

CROSS-REFERENCE TO RELATED APPLICATIONS

This application claims the priority benefit to U.S. Provisional No. 61/346,419 filed May 19, 2010, the entirety of which is hereby incorporated by reference herein.

BACKGROUND OF THE INVENTION

1. Field of the Invention

The present invention related to medical methods and devices, and, in particular, to an inflation media formulation and the method for using the same for inflatable medical devices, such as percutaneous implants having a formed in place support structure.

2. Description of the Related Art

According to recent estimates, more than 79,000 patients are diagnosed with aortic and mitral valve disease in U.S. hospitals each year. More than 49,000 mitral valve or aortic valve replacement procedures are performed annually in the U.S., along with a significant number of heart valve repair procedures.

The circulatory system is a closed loop bed of arterial and venous vessels supplying oxygen and nutrients to the body extremities through capillary beds. The driver of the system is the heart providing correct pressures to the circulatory system and regulating flow volumes as the body demands. Deoxygenated blood enters heart first through the right atrium and is allowed to the right ventricle through the tricuspid valve. Once in the right ventricle, the heart delivers this blood through the pulmonary valve and to the lungs for a gaseous exchange of oxygen. The circulatory pressures carry this blood back to the heart via the pulmonary veins and into the left atrium. Filling of the left atrium occurs as the mitral valve opens allowing blood to be drawn into the left ventricle for expulsion through the aortic valve and on to the body extremities. When the heart fails to continuously produce normal flow and pressures, a disease commonly referred to as heart failure occurs.

Heart failure simply defined is the inability for the heart to produce output sufficient to demand. Mechanical complications of heart failure include free-wall rupture, septal-rupture, papillary rupture or dysfunction aortic insufficiency and tamponade. Mitral, aortic or pulmonary valve disorders lead to a host of other conditions and complications exacerbating heart failure further. Other disorders include coronary disease, hypertension, and a diverse group of muscle diseases referred to as cardiomyopothies. Because of this syndrome establishes a number of cycles, heart failure begets more heart failure.

Heart failure as defined by the New York Heart Association in a functional classification.

I. Patients with cardiac disease but without resulting limitations of physical activity. Ordinary physical activity does not cause undue fatigue, palpitation, dyspnea, or anginal pain.

II. Patient with cardiac disease resulting in slight limitation of physical activity. These patients are comfortable at rest. Ordinary physical activity results in fatigue, palpitation, dyspnea, or anginal pain.

III. Patients with cardiac disease resulting in marked limitation of physical activity. These patients are comfortable at rest. Less than ordinary physical activity causes fatigue palpitation, dyspnea, or anginal pain.

IV. Patients with cardiac disease resulting in inability to carry on any physical activity without discomfort. Symptoms of cardiac insufficiency or of the anginal syndrome may be present even at rest. If any physical activity is undertaken, discomfort is increased.

There are many styles of mechanical valves that utilize both polymer and metallic materials. These include single leaflet, double leaflet, ball and cage style, slit-type and emulated polymer tricuspid valves. Though many forms of valves exist, the function of the valve is to control flow through a conduit or chamber. Each style will be best suited to the application or location in the body it was designed for.

Bioprosthetic heart valves comprise valve leaflets formed of flexible biological material. Bioprosthetic valves or components from human donors are referred to as homografts and xenografts are from non-human animal donors. These valves as a group are known as tissue valves. This tissue may include donor valve leaflets or other biological materials such as bovine pericardium. The leaflets are sewn into place and to each other to create a new valve structure. This structure may be attached to a second structure such as a stent or cage or other prosthesis for implantation to the body conduit.

Implantation of valves into the body has been accomplished by a surgical procedure and has been attempted via percutaneous method such as a catheterization or delivery mechanism utilizing the vasculature pathways. Surgical implantation of valves to replace or repair existing valves structures include the four major heart valves (tricuspid, pulmonary, mitral, aortic) and some venous valves in the lower extremities for the treatment of chronic venous insufficiency. Implantation includes the sewing of a new valve to the existing tissue structure for securement. Access to these sites generally include a thoracotomy or a sternotomy for the patient and include a great deal of recovery time. An open-heart procedure can include placing the patient on heart bypass to continue blood flow to vital organs such as the brain during the surgery. The bypass pump will continue to oxygenate and pump blood to the body's extremities while the heart is stopped and the valve is replaced. The valve may replace in whole or repair defects in the patient's current native valve. The device may be implanted in a conduit or other structure such as the heart proper or supporting tissue surrounding the heart. Attachments methods may include suturing, hooks or barbs, interference mechanical methods or an adhesion median between the implant and tissue.

Although valve repair and replacement can successfully treat many patients with valvular insufficiency, techniques currently in use are attended by significant morbidity and mortality. Most valve repair and replacement procedures require a thoracotomy, usually in the form of a median sternotomy, to gain access into the patient's thoracic cavity. A saw or other cutting instrument is used to cut the sternum longitudinally, allowing the two opposing halves of the anterior or ventral portion of the rib cage to be spread apart. A large opening into the thoracic cavity is thus created, through which the surgical team may directly visualize and operate upon the heart and other thoracic contents. Alternatively, a thoracotomy may be performed on a lateral side of the chest, wherein a large incision is made generally parallel to the ribs, and the ribs are spread apart and/or removed in the region of the incision to create a large enough opening to facilitate the surgery.

Surgical intervention within the heart generally requires isolation of the heart and coronary blood vessels from the remainder of the arterial system, and arrest of cardiac function. Usually, the heart is isolated from the arterial system by introducing an external aortic cross-clamp through a sternotomy and applying it to the aorta to occlude the aortic lumen between the brachiocephalic artery and the coronary ostia. Cardioplegic fluid is then injected into the coronary arteries, either directly into the coronary ostia or through a puncture in the ascending aorta, to arrest cardiac function. The patient is placed on extracorporeal cardiopulmonary bypass to maintain peripheral circulation of oxygenated blood.

Since surgical techniques are highly invasive and in the instance of a heart valve, the patient must be put on bypass during the operation, the need for a less invasive method of heart valve replacement has long been recognized. At least as early as 1972, the basic concept of suturing a tissue aortic valve to an expandable cylindrical "fixation sleeve" or stent was disclosed. See U.S. Pat. No. 3,657,744 to Ersek. Other early efforts were disclosed in U.S. Pat. No. 3,671,979 to Moulopoulos and U.S. Pat. No. 4,056,854 to Boretos, relating to prosthetic valves carried by an expandable valve support delivered via catheter for remote placement. More recent iterations of the same basic concept were disclosed, for example, in patents such as U.S. Pat. Nos. 5,411,552, 5,957,949, 6,168,614, and 6,582,462 to Anderson, et al., which relate generally to tissue valves carried by expandable metallic stent support structures which are crimped to a delivery balloon for later expansion at the implantation site.

In each of the foregoing systems, the tissue or artificial valve is first attached to a preassembled, complete support structure (some form of a stent) and then translumenally advanced along with the support structure to an implantation site. The support structure is then forceably enlarged or allowed to self expand without any change in its rigidity or composition, thereby securing the valve at the site.

Despite the many years of effort, and enormous investment of entrepreneurial talent and money, no stent based heart valve system has yet received regulatory approval, and a variety of difficulties remain. For example, stent based systems have a fixed rigidity even in the collapsed configuration, and have inherent difficulties relating to partial deployment, temporary deployment, removal and navigation.

Thus, a need remains for improvements over the basic concept of a stent based prosthetic valve. As disclosed herein a variety of significant advantages may be achieved by eliminating the stent and advancing the valve to the site without a support structure. Only later, the support structure is created in situ such as by inflating one or more inflatable chambers or inflatable structures to impart rigidity to an otherwise highly flexible and functionless subcomponent.

SUMMARY OF THE INVENTION

One embodiment provides an inflatable implant comprises at least one inflation channel for forming an inflatable structure of the inflatable implant; and an inflation media disposed within the at least one inflation channel, wherein the inflation media comprises a mixture of an epoxy resin and a hardener, the mixture is configured to have an average viscosity of less than about 100 cps at about 37° C. over the first 10 minutes after mixing, and gel at about 37° C. in less than about 2.5 hours after mixing to form a gelled mixture.

One embodiment provides an inflation media comprising an epoxy resin comprising a first compound having at least one N,N-bis(oxiran-2-ylmethyl)aniline segment and a second compound having at least two oxirane groups on a backbone of no more than five carbons; and a hardener comprising at least one cycloaliphatic amine.

One embodiment provides a prosthetic valve implant delivery system comprising a deployment catheter comprising an inflation tube and a prosthetic valve comprising an inflatable structure in communication with the inflation tube; and an inflation media as disclosed herein for inflating the inflatable structure through the inflation tube.

One embodiment provides a method of implanting a prosthetic valve within the heart, the method comprising translumenally advancing a prosthetic valve comprising an inflatable structure to a position proximate a native valve of the heart, mixing the epoxy resin and the hardener in the inflation media disclosed herein to form an epoxy mixture; and inflating the inflatable structure with the epoxy mixture.

One embodiment provides a method of treating a patient, comprising advancing a deployment catheter to a position proximate a native valve of the heart, the deployment catheter comprising an inflation tube and a prosthetic valve comprising an inflatable structure in communication with the inflation tube; deploying the prosthetic valve at the cardiovascular site; inflating the inflatable structure with an epoxy mixture comprising the inflation media disclosed herein through the inflation tube; and detaching the deployment catheter from the prosthetic valve and removing the deployment catheter from the patient.

BRIEF DESCRIPTION OF THE DRAWINGS

FIG. 8B is a cross-sectional view taken through line 36B-36B of FIG. 8A.

FIGS. 10A-C are time sequenced steps of an embodiment of a method for deploying a prosthetic valve implant.

DETAILED DESCRIPTION OF THE PREFERRED EMBODIMENTS

Figure 1:
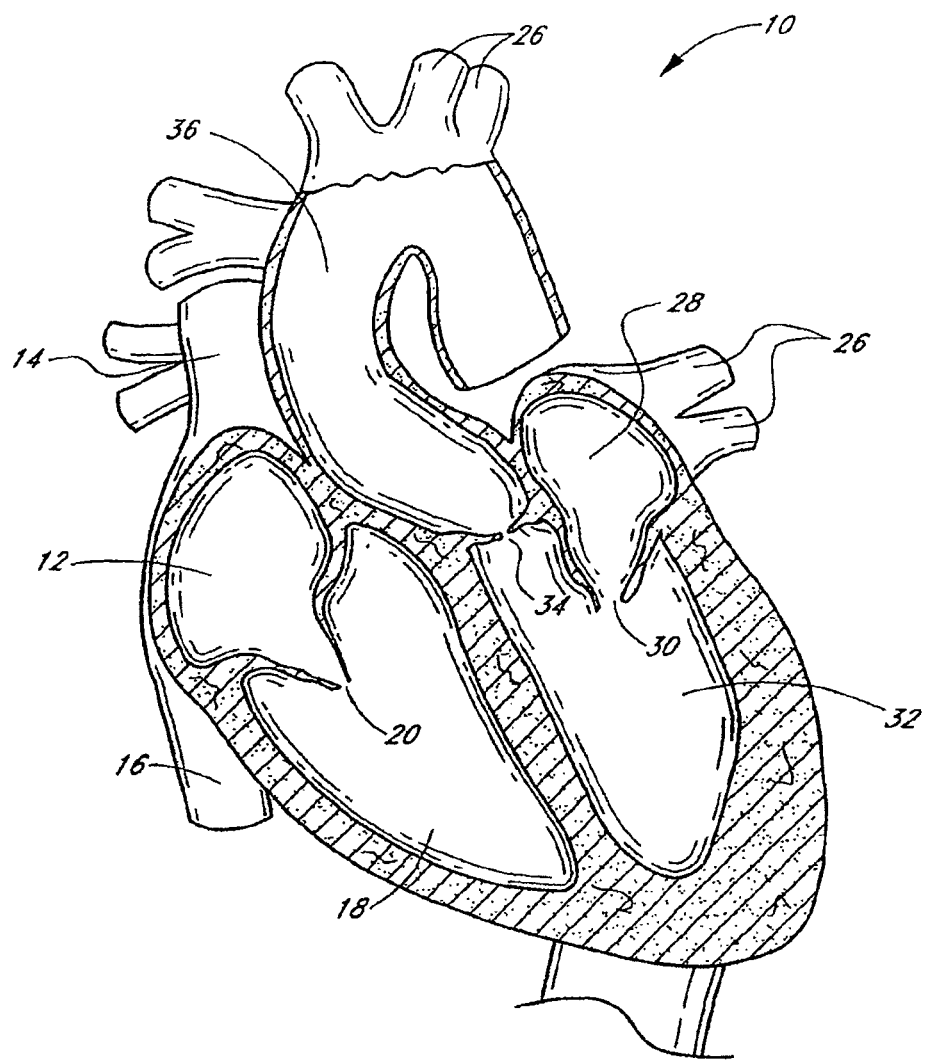
FIG. 1 is a cross-sectional schematic view of a heart and its major blood vessels.

FIG. 1 is a schematic cross-sectional illustration of the anatomical structure and major blood vessels of a heart 10. Deoxygenated blood is delivered to the right atrium 12 of the heart 10 by the superior and inferior vena cava 14, 16. Blood in the right atrium 12 is allowed into the right ventricle 18 through the tricuspid valve 20. Once in the right ventricle 18, the heart 10 delivers this blood through the pulmonary valve 22 to the pulmonary arteries 24 and to the lungs for a gaseous exchange of oxygen. The circulatory pressures carry this blood back to the heart via the pulmonary veins 26 and into the left atrium 28. Filling of the left atrium 28 occurs as the mitral valve 30 opens allowing blood to be drawn into the left ventricle 32 for expulsion through the aortic valve 34 and on to the body extremities through the aorta 36. When the heart 10 fails to continuously produce normal flow and pressures, a disease commonly referred to as heart failure occurs.

One cause of heart failure is failure or malfunction of one or more of the valves of the heart 10. For example, the aortic valve 34 can malfunction for several reasons. For example, the aortic valve 34 may be abnormal from birth (e.g., bicuspid, calcification, congenital aortic valve disease), or it could become diseased with age (e.g., acquired aortic valve disease). In such situations, it can be desirable to replace the abnormal or diseased valve 34.

Figure 2:
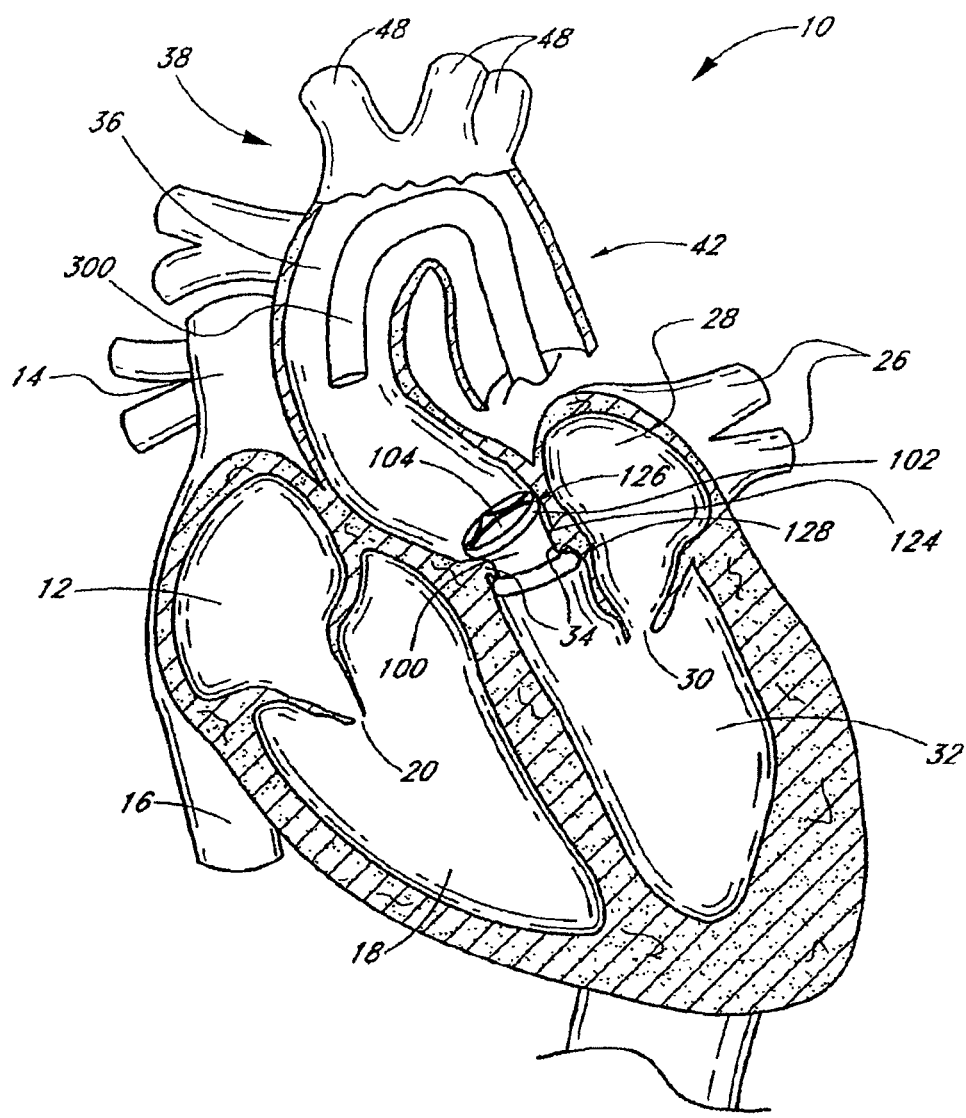
FIG. 2 is a partial cut-away view a left ventricle and aortic with an prosthetic aortic valve implant according to one embodiment.

FIG. 2 is a schematic illustration of the left ventricle 32, which delivers blood to the aorta 36 through the aortic valve 34. The aorta 36 comprises (i) the ascending aorta 38, which arises from the left ventricle 32 of the heart 10, (ii) the aortic arch 10, which arches from the ascending aorta 38 and (iii) the descending aorta 42 which descends from the aortic arch 40 towards the abdominal aorta (not shown). Also shown are the principal branches of the aorta 14, which include the innomate artery 44 that immediately divides into the right carotid artery (not shown) and the right subclavian artery (not shown), the left carotid 46 and the subclavian artery 48.

Inflatable Prosthetic Aortic Valve Implant

With continued reference to FIG. 2, a prosthetic aortic valve implant 100 in accordance with one embodiment is shown spanning the native abnormal or diseased aortic valve 34, which has been partially removed as will be described in more detail below. The implant 100 and various modified embodiments thereof will be described in detail below. As will be explained in more detail below, the implant 100 is preferably delivered minimally invasively using an intravascular delivery catheter 200 or trans apical approach with a trocar.

In the description below, the present invention will be described primarily in the context of replacing or repairing an abnormal or diseased aortic valve 34. However, various features and aspects of methods and structures disclosed herein are applicable to replacing or repairing the mitral 30, pulmonary 22 and/or tricuspid 20 valves of the heart 10 as those of skill in the art will appreciate in light of the disclosure herein. In addition, those of skill in the art will also recognize that various features and aspects of the methods and structures disclosed herein can be used in other parts of the body that include valves or can benefit from the addition of a valve, such as, for example, the esophagus, stomach, ureter and/or vesice, biliary ducts, the lymphatic system and in the intestines.

In addition, various components of the implant and its delivery system will be described with reference to coordinate system comprising "distal" and "proximal" directions. In this application, distal and proximal directions refer to the deployment system 300, which is used to deliver the implant 100 and advanced through the aorta 36 in a direction opposite to the normal direction of blood through the aorta 36. Thus, in general, distal means closer to the heart while proximal means further from the heart with respect to the circulatory system.

With reference now to FIGS. 3A-G, the implant 100 of the illustrated embodiment generally comprises an inflatable cuff or body 102, which is configured to support a valve 104 (see FIG. 2) that is coupled to the cuff 102. As will be explained in more detail below, the valve 104 is configured to move in response to the hemodynamic movement of the blood pumped by the heart 10 between an "open" configuration where blood can throw the implant 100 in a first direction and a "closed" configuration whereby blood is prevented from back flowing through the valve 104 in a second direction.

In the illustrated embodiment, the cuff 102 comprises a thin flexible tubular material 106 such as a flexible fabric or thin membrane with little dimensional integrity. As will be explained in more detail below, the cuff 102 can be changed preferably, in situ, to a support structure to which other components (e.g., the valve 104) of the implant 100 can be secured and where tissue ingrowth can occur. Uninflated, the cuff 102 is preferably incapable of providing support. In one embodiment, the cuff 102 comprises Dacron, PTFE, ePTFE, TFE or polyester fabric 106 as seen in conventional devices such as surgical stented or stent less valves and annuloplasty rings. The fabric 106 thickness may range from about 0.002 inches to about 0.020 inches of an inch depending upon material selection and weave. Weave density may also be adjusted from a very tight weave to prevent blood from penetrating through the fabric 106 to a looser weave to allow tissue to grow and surround the fabric 106 completely. Additional compositions and configurations of the cuff 102 will be described in more detail below.

Figure 3A:
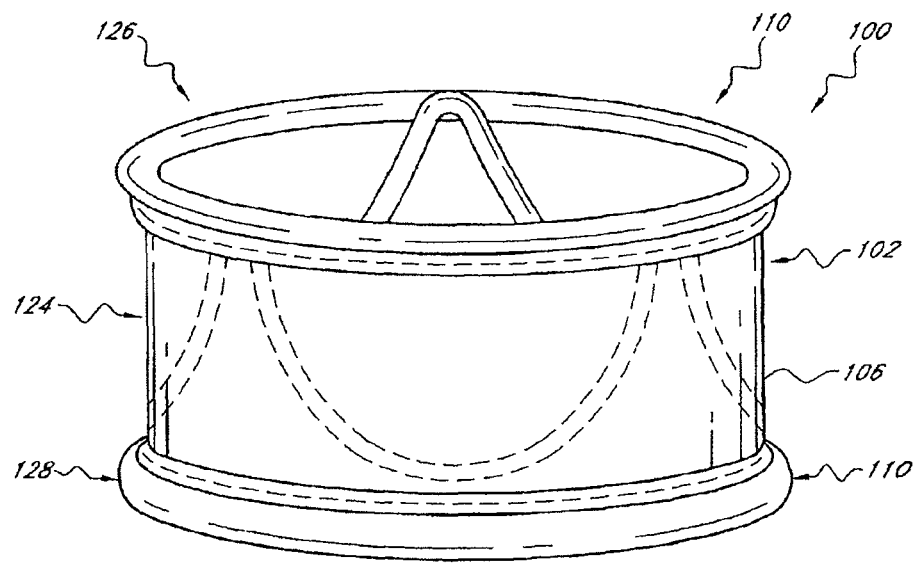
FIG. 3A is a front perspective view of the implant of FIG. 2.
Figure 3B:
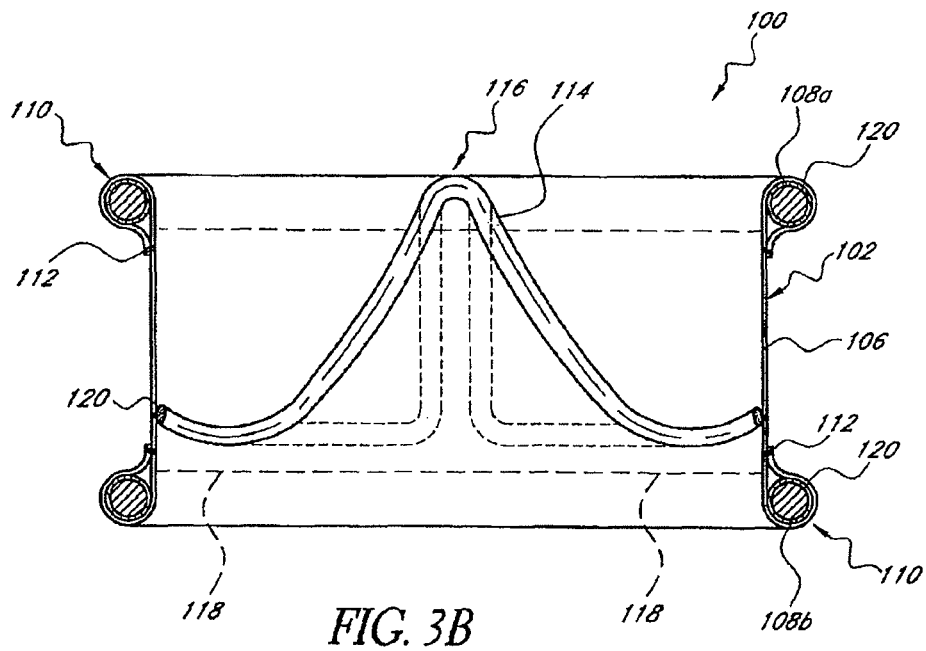
FIG. 3B is a cross-sectional side view of the implant of FIG. 3A.
Figure 3C:
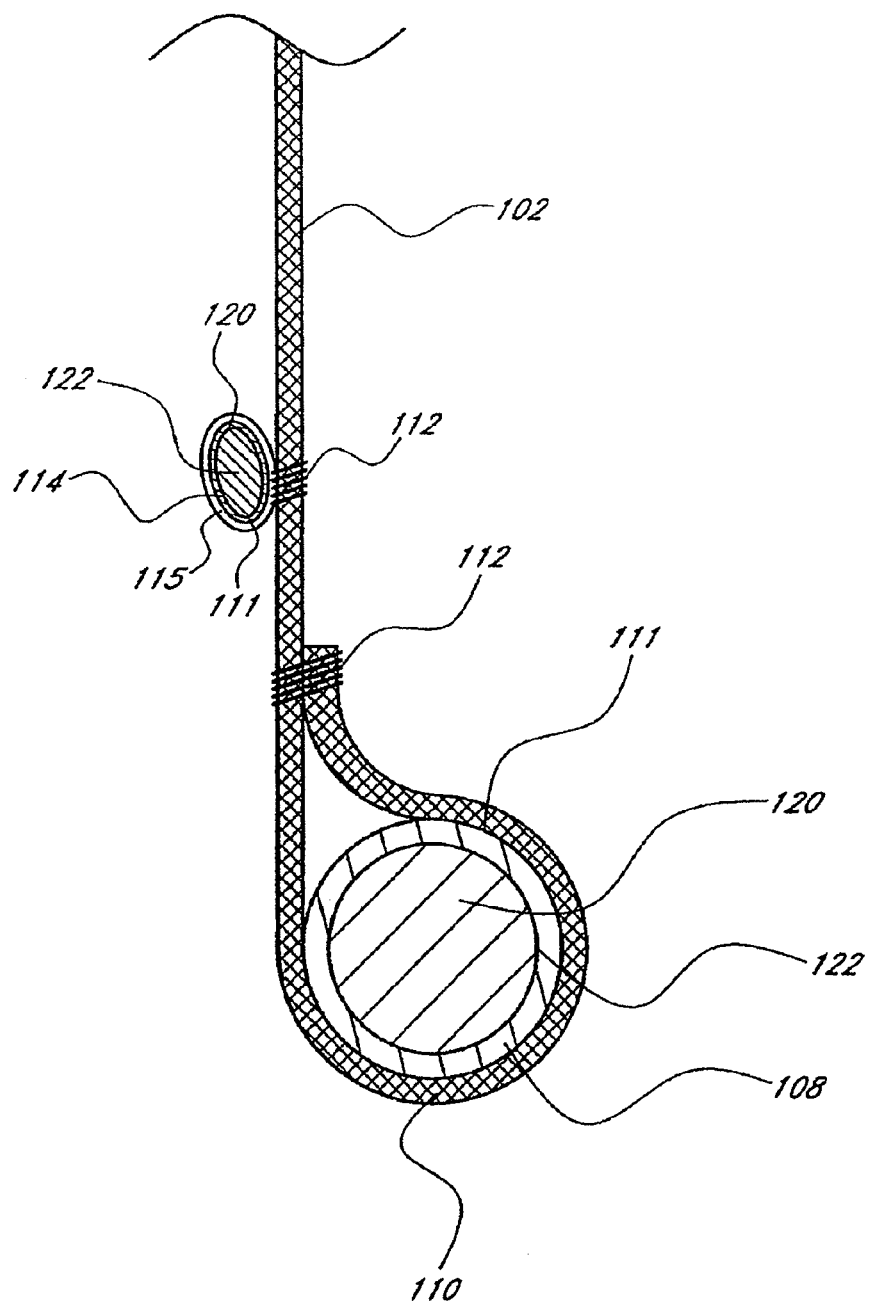
FIG. 3C is an enlarged cross-sectional view of a lower portion of FIG. 3B.
Figure 3D:
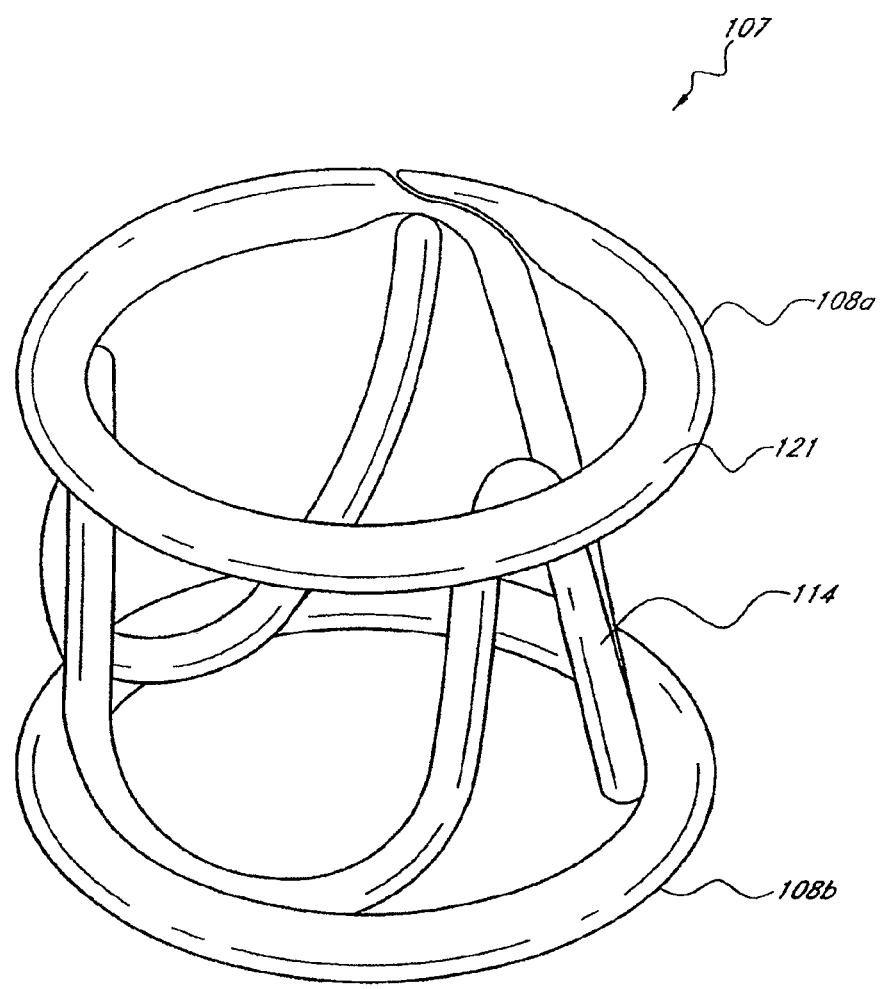
FIG. 3D is a front perspective view of an inflatable support structure of the implant of FIG. 3A.

With continued reference to FIGS. 3B-3D, in the illustrated embodiment, the implant 100 includes an inflatable structure 107 that forms one or more of inflation channels 120, which in illustrated embodiment are formed in part by a pair of distinct balloon rings or toroids 108a, 108b. The rings 108a, 108b in this embodiment are positioned at the proximal and distal ends 126, 128 of the cuff 102. As will be explained below, the rings 108 can be secured to the body 102 in any of a variety of manners. With reference to FIG. 3C, in the illustrated embodiment, the rings 108 are secured within folds 110 formed at the proximal and distal ends 126, 128 of the cuff 102. The folds 110, in turn, are secured by sutures or stitches 112. See FIG. 3C.

The illustrated inflatable structure 107 also includes inflatable struts 114, which in the illustrated embodiment are formed from an annular zig-zag pattern having three proximal bends 116 and three distal bends 118. As best seen in FIG. 3C, the struts 114 can be secured to the cuff 102 within pockets 115 of cuff material by sutures 112. Of course, as will be explained in more detail, other embodiments other configurations can be can be used to secure the struts 114 to the fabric 106.

As mentioned above, the inflatable rings 108 (i.e., toroids) and struts 114 form the inflatable structure 107, which, in turn, defines the inflation channels 120. The inflation channels 120 receive inflation media 122 to generally inflate the inflatable structure 107. When inflated, the inflatable rings and struts 108, 114 provide can provide structural support to the inflatable implant 100 and/or help to secure the implant 100 within the heart 10. Uninflated, the implant 100 is a generally thin, flexible shapeless assembly that is preferably uncapable of support and is advantageously able to take a small, reduced profile form in which it can be percutaneously inserted into the body. As will be explained in more detail below, in modified embodiments, the inflatable structure 107 may comprise any of a variety of configurations of inflation channels 120 that can be formed from other inflatable members in addition to or in the alternative to the inflatable rings 108 and struts 114 shown in FIGS. 3A and 3B. In addition, the inflatable media 122 and methods for inflating the inflatable structure 107 will be described in more detail below.

With particular reference to FIG. 3D, in the illustrated embodiment, the proximal ring 108a and struts 114 are joined such that the inflation channel 120 of the proximal ring 108a is in fluid communication with the inflation channel 120 of the struts 114. In contrast, the inflation channel 120 of the distal ring 108b is not in communication with the inflation channels 120 of the proximal ring 108a and struts 114. In this manner, the inflation channels of the (i) proximal ring 108a and struts 114 can be inflated independently from the (ii) distal ring 108b. As will be explained in more detail below, the two groups of inflation channels 120 are preferably connected to independent fluid delivery devices to facilitate the independent inflation. It should be appreciated that in modified embodiments the inflatable structure can include less (i.e., one common inflation channel) or more independent inflation channels. For example, in one embodiment, the inflation channels of the proximal ring 108a, struts 114 and distal ring 108b can all be in fluid communication with each other such that they can be inflated from a single inflation device. In another embodiment, the inflation channels of the proximal ring the proximal ring 108a, struts 114 and distal ring 108b can all be separated and therefore utilize three inflation devices.

With reference to FIG. 3B, in the illustrated embodiment, the proximal ring 108a has a cross-sectional diameter of about 0.090 inches. The struts have a cross-sectional diameter of about 0.060 inches. The distal ring 108b has a cross-sectional diameter of about 0.090 inches diameter.

Figure 3E:
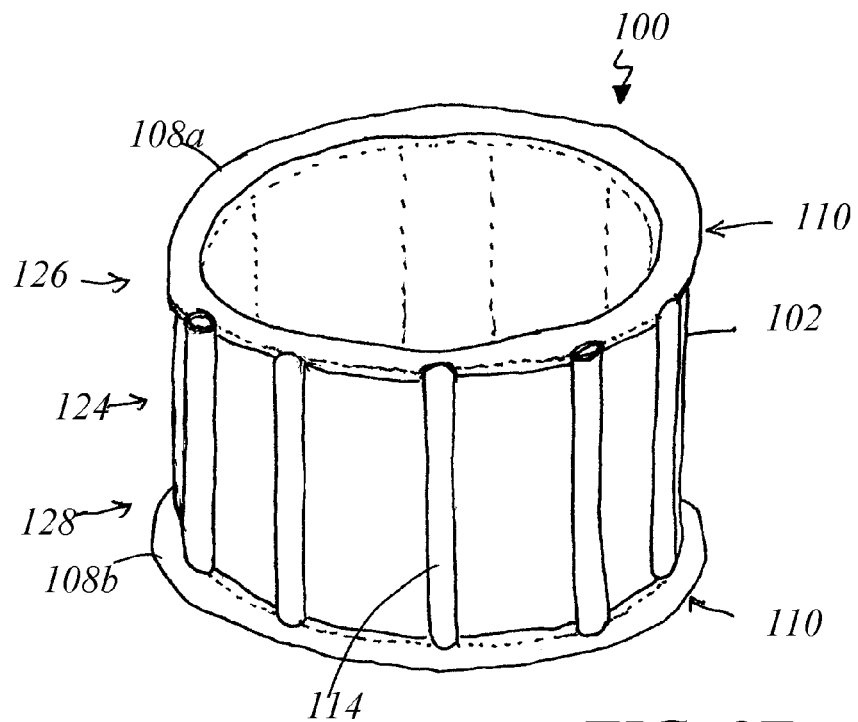
FIG. 3E is a front perspective view of an implant.

With reference to FIG. 3E, the implant 100 of the illustrated embodiment generally comprises an inflatable cuff or body 102, which is configured to support a valve 104 that is coupled to the cuff 102. In some embodiments, the valve 104 is a tissue valve. In some embodiments, the tissue valve has a thickness equal to or greater than about 0.011 inches. In another embodiment, the tissue valve has a thickness equal to or greater than about 0.018 inches. As will be explained in more detail below, the valve 104 is configured to move in response to the hemodynamic movement of the blood pumped by the heart between an "open" configuration where blood can throw the implant 100 in a first direction and a "closed" configuration whereby blood is prevented from back flowing through the valve 104 in a second direction.

In the illustrated embodiment, the cuff 102 comprises a thin flexible tubular material such as a flexible fabric or thin membrane with little dimensional integrity. As will be explained in more detail below, the cuff 102 can be changed preferably, in situ, to a support structure to which other components (e.g., the valve 104) of the implant 100 can be secured and where tissue ingrowth can occur. Uninflated, the cuff 102 is preferably incapable of providing support. In one embodiment, the cuff 102 comprises Dacron, PTFE, ePTFE, TFE or polyester fabric as seen in conventional devices such as surgical stented or stent less valves and annuloplasty rings. The fabric thickness may range from about 0.002 inches to about 0.020 inches depending upon material selection and weave. Weave density may also be adjusted from a very tight weave to prevent blood from penetrating through the fabric to a looser weave to allow tissue to grow and surround the fabric completely. In preferred embodiments, the fabric may have a linear mass density about 20 denier or lower.

Figure 3F:
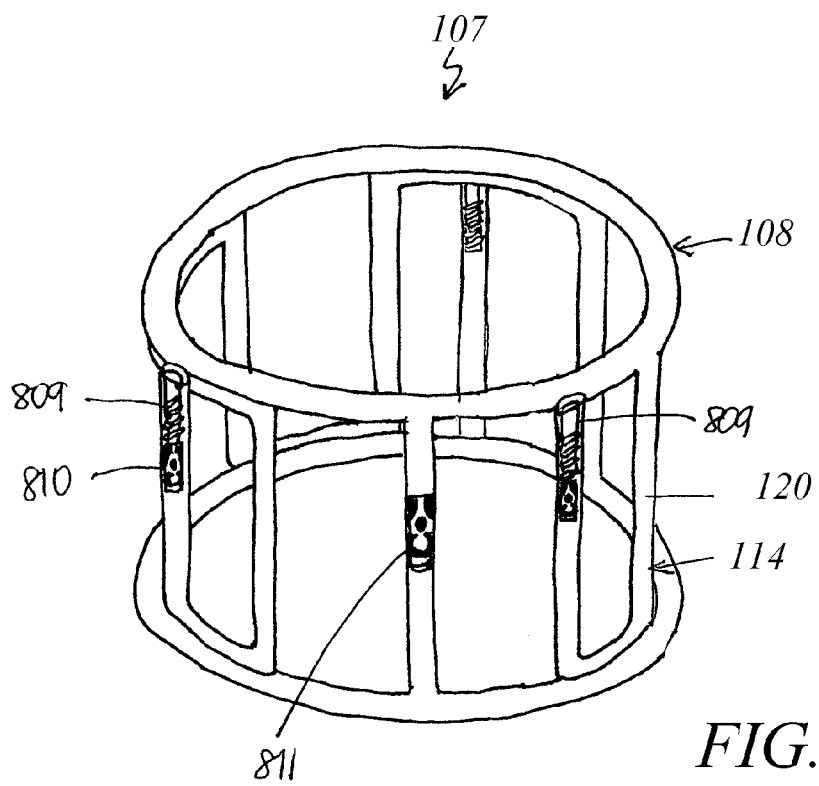
FIG. 3F is a front perspective view of an inflatable support structure of the implant of FIG. 3E.
Figure 3G:
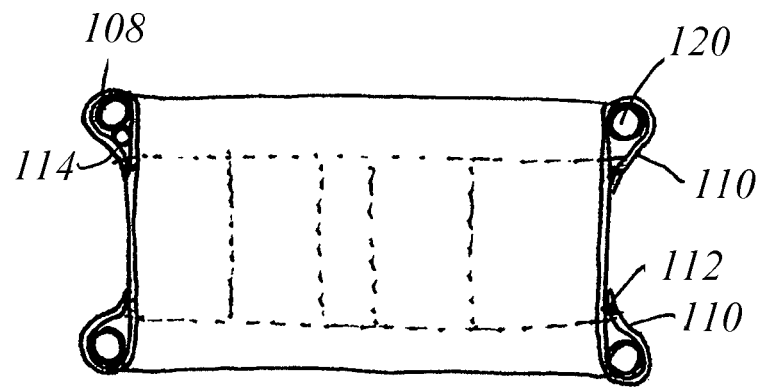
FIG. 3G is a cross-sectional side view of the implant of FIG. 3E.
Figure 3H:
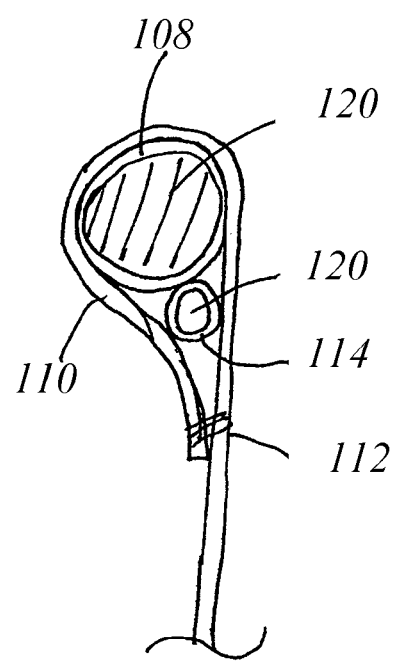
FIG. 3H is an enlarged cross-sectional view of an upper portion of FIG. 3G

With reference to FIGS. 3F-3H, in the illustrated embodiment, the implant 100 includes an inflatable structure 107 that is formed by one or more inflation channels 120. The inflatable channels 120 are formed by a pair of distinct balloon rings or toroids (108a and 108b) and struts 114. In the illustrated embodiment, the implant 100 comprises a proximal toroid 108a at the proximal end 126 of the cuff 102 and a distal toroid 108b at the distal end 128 of the cuff 102. The toroids 108 can be secured to the cuff 102 in any of a variety of manners. With reference to FIGS. 3G and 3H, in the illustrated embodiment, the toroids 108 are secured within folds 110 formed at the proximal end 126 and the distal end 128 of the cuff 102. The folds 110, in turn, are secured by sutures or stitches 112. When inflated, the implant 100 is supported in part by series of struts 114 surrounding the cuff 102. In some embodiments, the struts 114 are configured so that the portions on the cuff run substantially perpendicular to the toroids. In some embodiments, the struts are sewn onto the cuff 102 or are enclosed in lumens made from the cuff material and swan onto the cuff 102. The toroids 108 and the struts 114 together form one or more inflatable channels 120 that can be inflated by air, liquid or inflation media.

With reference to FIG. 3F, the inflation channels are configured so that the cross-sectional profile of the implant 100 is reduced when it is compressed or in the retracted state. The inflation channels 120 are arranged in a step-function pattern. The inflation channels 120 have three connection ports 809 for coupling to the delivery catheter 300 via position and fill lumen tubing (PFL) 320. In some embodiments, at least two of the connection ports 809 also function as inflation ports, and inflation media, air or liquid can be introduced into the inflation channel 120 through these ports. The PFL tubing 320 can be connected to the connection ports 809 via suitable connection mechanisms. In one embodiment, the connection between the PFL tubing 320 and the connection port 809 is a screw connection. In some embodiments, an inflation valve 810 is present in the connection port 809 and can stop the inflation media, air or liquid from escaping the inflation channels 120 after the PFL tubing is disconnected. In some embodiments, the distal toroid 108b and the proximal toroid 108a may be inflated independently. In some embodiments, the distal toroid 108b can be inflated separately from the struts 114 and the proximal toroid 108a. The separate inflation is useful during the positioning of the implant at the implantation site. With reference to FIGS. 3G and 3H, in some embodiments, the portion of struts 114 that runs parallel to the toroids 108 is encapsulated within the folds 110 of the implant 100. This may also aid in reducing the cross-sectional profile when the implant is compressed or folded.

As mentioned above, the inflatable rings or toroids 108 and struts 114 form the inflatable structure 107, which, in turn, defines the inflation channels 120. The inflation channels 120 receive inflation media to generally inflate the inflatable structure 107. When inflated, the inflatable rings 108 and struts 114 can provide structural support to the inflatable implant 100 and/or help to secure the implant 100 thin the heart 10. Uninflated, the implant 100 is a generally thin, flexible shapeless assembly that is preferably uncapable of support and is advantageously able to take a small, reduced profile form in which it can be percutaneously inserted into the body. As will be explained in more detail below, in modified embodiments, the inflatable structure 107 may comprise any of a variety of configurations of inflation channels 120 that can be formed from other inflatable members in addition to or in the alternative to the inflatable rings 108 and struts 114 shown in FIGS. 3E and 3F. In one embodiment, the valve has an expanded diameter that is greater than or equal to 22 millimeters and a maximum compressed diameter that is less than or equal to 6 millimeters (18F).

With particular reference to FIG. 3F, in the illustrated embodiment, the distal ring 108b and struts 114 are joined such that the inflation channel 120 of the distal ring 108b is in fluid communication with the inflation channel 120 of some of the struts 114. The inflation channel 120 of the proximal ring 108a is also in communication with a few of the struts 114. In this manner, the inflation channels of the (i) proximal ring 108a and a few struts 114 can be inflated independently from the (ii) distal ring 108b and some struts. In some embodiments, the inflation channel of the proximal ring 108a is in communication with the inflation channel of the struts 114, while the inflation channel of the distal ring 108b is not in communication with the inflation channel of the struts. As will be explained in more detail below, the two groups of inflation channels 120 are preferably connected to independent PFL tubing 320 to facilitate the independent inflation. It should be appreciated that in modified embodiments the inflatable structure can include less (i.e., one common inflation channel) or more independent inflation channels. For example, in one embodiment, the inflation channels of the proximal ring 108a, struts 114 and distal ring 108b can all be in fluid communication with each other such that they can be inflated from a single inflation device. In another embodiment, the inflation channels of the proximal ring 108a, struts 114 and distal ring 108b can all be separated and therefore utilize three inflation devices.

With reference to FIG. 3F, in the illustrated embodiment, each of the proximal ring 108a and the distal ring 108b has a cross-sectional diameter of about 0.090 inches. The struts have a cross-sectional diameter of about 0.060 inches. In some embodiments, within the inflation channels 120 are also housed valve systems that allow for pressurization without leakage or passage of fluid in a single direction. In the illustrated embodiment shown in FIG. 3F, two end valves or inflation valves 810 reside at each end section of the inflation channels 120 adjacent to the connection ports 809. These end valves 810 are utilized to fill and exchange fluids such as saline, contrast agent and inflation media. The length of this inflation channel 120 may vary depending upon the size of the implant 100 and the complexity of the geometry. The inflation channel material may be blown using heat and pressure from materials such as nylon, polyethylene, Pebax, polypropylene or other common materials that will maintain pressurization. The fluids that are introduced are used to create the support structure, where without them, the implant 100 is an undefined fabric and tissue assembly. In one embodiment the inflation channels 120 are first filled with saline and contrast agent for radiopaque visualization under fluoroscopy. This can make positioning the implant 100 at the implantation site easier. This fluid is introduced from the proximal end of the catheter 300 with the aid of an inflation device such as an endoflator or other means to pressurize fluid in a controlled manner. This fluid is transferred from the proximal end of the catheter 300 through the PFL tubes 320 which are connected to the implant 100 at the end of each inflation channel 120 at the connection port 809.

With reference to FIG. 3F, in the illustrated embodiment, the inflation channel 120 can have an end valve 810 (i.e., inflation valve) at each end whereby they can be separated from the PFL tubes 320 thus disconnecting the catheter from the implant. This connection can be a screw or threaded connection, a collecting system, an interference fit or other means of reliable securement between the two components (i.e., the end valve 810 and the PFL tubes 320). In between the ends of the inflation channel 120 is an additional directional valve 811 to allow fluid to pass in a single direction. This allows for the filling of each end of the inflation channel 120 and displacement of fluid in a single direction. Once the implant 120 is placed at the desired position while inflated with saline and contrast agent, this fluid can be displaced by an inflation media that can solidify or harden. As the inflation media is introduced from the proximal end of the catheter 300, the fluid containing saline and contrast agent is pushed out from one end of the inflation channel 120. Once the inflation media completely displaces the first fluid, the PFL tubes 320 are then disconnected from the implant 100 while the implant 100 remains inflated and pressurized. The pressure is maintained in the implant 100 by the integral valve (i.e., end valve 810) at each end of the inflation channel 120. In the illustrated embodiment, this end valve 810 has a ball 303 and seat to allow for fluid to pass when connected and seal when disconnected. In some case the implant 100 has three or more connection ports 809, but only two have inflation valves 810 attached. The connection port without the end valve 810 may use the same attachment means such as a screw or threaded element. Since this connection port is not used for communication with the support structure 107 and its filling, no inflation valve 810 is necessary. In other embodiments, all three connection ports 809 may have inflation valves 810 for introducing fluids or inflation media.

In prior art surgically implanted valves, the valve generally includes a rigid inner support structure that is formed from polycarbonate, silicone or titanium wrapped in silicone and Dacron. These surgical valves vary in diameter for different patients due to the respective implantation site and orifice size. Generally the largest diameter implantable is the best choice for the patient. These diameters range from about 16 mm to 30 mm.

As mentioned above, the implant 100 allows the physician to deliver a valve via catheterization in a lower profile and a safer manner than currently available. When the implant 100 is delivered to the site via a delivery catheter 300 (see FIG. 6), the implant 100 is a thin, generally shapeless assembly in need of structure and definition. At the implantation site, the inflation media 122 (e.g., a fluid or gas) may be added via a catheter lumen to the inflation channels 120 providing structure and definition to the implant 100. The inflation media 122 therefore comprises part of the support structure for implant 100 after it is inflated. The inflation media 122 that is inserted into the inflation channels 120 can be pressurized and/or can solidify in situ to provide structure to the implant 100. Additional details and embodiments of the implant 100, can be found in U.S. Pat. No. 5,554,185 to Block and co-pending U.S. patent application titled "Low Crossing Profile Delivery Catheter for Cardiovascular Prosthetic Implant," the disclosures of which are expressly incorporated in their entireties herein by reference.

With reference back to FIGS. 3A, 3B, and 3E, the body 102 may be made from many different materials such as Dacron, TFE, PTFE, ePTFE, woven metal fabrics, braided structures, or other generally accepted implantable materials. These materials may also be cast, extruded, or seamed together using heat, direct or indirect, sintering techniques, laser energy sources, ultrasound techniques, molding or thermoforming technologies. Since the body 102 generally surrounds the inflation lumens 120, which can be formed by separate members (e.g., rings 108), the attachment or encapsulation of these lumens 120 can be in intimate contact with the body material 106 or a loosely restrained by the surrounding material 106. These inflation lumens 120 can also be formed also by sealing the body material 106 to create an integral lumen from the body 102 itself. For example, by adding a material such as a silicone layer to a porous material such as Dacron, the fabric 106 can resist fluid penetration or hold pressures if sealed. Materials may also be added to the sheet or cylinder material to create a fluid tight barrier. However, in the illustrated embodiment of FIGS. 3A and 3B, the inflation lumens 120 are formed by balloons 111 (see FIG. 3C), which form the separate inflation components 108a, 108b, 122, which are, in turn, secured to the material 106.

Various shapes of the body 102 may be manufactured to best fit anatomical variations from person to person. As described above, these may include a simple cylinder, a hyperboloid, a device with a larger diameter in its mid portion and a smaller diameter at one or both ends, a funnel type configuration or other conforming shape to native anatomies. The shape of the implant 100 is preferably contoured to engage a feature of the native anatomy in such a way as to prevent the migration of the device in a proximal or distal direction. In one embodiment the feature that the device engages is the aortic root or aortic bulb 34, or the sinuses of the coronary arteries. In another embodiment the feature that the device engages is the native valve annulus, the native valve or a portion of the native valve. In certain embodiments, the feature that the implant 100 engages to prevent migration has a diametral difference between 1% and 10%. In another embodiment the feature that the implant 100 engages to prevent migration the diameter difference is between 5% and 40%. In certain embodiments the diameter difference is defined by the free shape of the implant 100. In another embodiment the diameter difference prevents migration in only one direction. In another embodiment, the diameter difference prevents migration in two directions, for example proximal and distal or retrograde and antigrade. Similar to surgical valves, the implant 100 will vary in diameter ranging from about 14 mm to about 30 mm and have a height ranging from about 10 mm to about 30 mm in the portion of the implant 100 where the leaflets of the valve 104 are mounted. Portions of the implant 100 intended for placement in the aortic root may have larger diameters preferably ranging from about 20 to about 45 mm Different diameters of valves will be required to replace native valves of various sizes. For different locations in the anatomy, different lengths of valves or anchoring devices will also be required. For example a valve designed to replace the native aortic valve needs to have a relatively short length because of the location of the coronary artery ostium (left and right arteries). A valve designed to replace or supplement a pulmonary valve could have significantly greater length because the anatomy of the pulmonary artery allows for additional length.

Inflation Media

The inflatable structure 107 can be inflated using any of a variety of inflation media 122, depending upon the desired performance. In general, the inflation media can include a liquid such as water or an aqueous based solution, a gas such as $CO_2$, or a hardenable media which may be introduced into the cuff 102 at a first, relatively low viscosity and converted to a second, relatively high viscosity. Viscosity enhancement may be accomplished through any of a variety of known UV initiated or catalyst initiated polymerization reactions, or other chemical systems known in the art. The end point of the viscosity enhancing process may result in hardness anywhere from a gel to a rigid structure, depending upon the desired performance and durability. In some embodiments, the resulting hardened inflation media may be in a semi-solid state. The term "semi-solid state" refers to a state of the fluid that is between the liquid and the solid states.

Useful inflation media generally include those formed by the mixing of multiple components and that have a gel time ranging from tens of minutes to a few hours, preferably from about one to about four hours. The gel time is the time it takes for the inflation media to solidify to the point that if the inflation channel or lumen is cut open to expose the cross section, the inflation media stays in the lumen and does not spill out for at least a few minutes. In some embodiments, the solidified inflation media stays in the lumen for at least about 2, 3, 4 or 5 minutes without spilling out. In some embodiments, the solidified inflation media stays in the lumen for at least 30, 45 or 60 minutes.

In some embodiments, such a material exhibits long-term stability (preferably on the order of at least 3 years, at least 5 years, at least 8 years or at least 10 years in vivo). In some embodiments, the desirable inflation media would exhibit adequate mechanical properties, both pre and post-cure, suitable for service in the cuff of the present invention in vivo. For instance, such a material should have a relatively low viscosity before solidification or curing to facilitate the cuff and channel fill process. A desirable post-cure elastic modulus of such an inflation medium is from about 50 psi to about 400 psi—balancing the need for the filled body to form an adequate seal in vivo while maintaining clinically relevant kink resistance of the cuff. In some embodiments, the inflation media is preferably radiopaque, both acute and chronic, although this is not absolutely necessary. In some embodiment, the inflation media also poses low embolic risk to the patient who receives the implant that is inflated with the inflation media disclosed herein.

Some embodiments provide an epoxy blend that can be used as an inflation media for inflating an inflatable structure of a medical device. In accordance with certain embodiments, preferred inflation media have the following characteristics: (1) low viscosity for catheter delivery, especially when the catheter has a small inner diameter, such as 18 French or less; (2) minimal toxicity and good water solubility in case there is an accidental spill during the delivery; (3) short curing time at body temperature, without significantly raising the temperature during curing; and (4) radio-opacity to allow fluoroscopic imaging during delivery. Once the inflation media is mixed, delivered to the inflatable structure and hardened, the hardened inflation media (1) has a long term mechanical performance in an aqueous environment including fatigue and creep, and (2) is chemically stable in aqueous and biological environments.

In some embodiments, the inflation media is a hardenable 2 part epoxy comprising an epoxy resin and a hardener. The epoxy resin and the hardener are mixed to form an epoxy mixture, which then harden into a high viscous gel, semi-solid or solid for structural support in the inflatable medical device. The epoxy resin comprises a first aromatic diepoxy compound and a second aliphatic diepoxy compound. The first aromatic diepoxy compound provides good mechanical and chemical stability in an aqueous environment while being soluble in aqueous solution when combined with suitable aliphatic epoxies. In some embodiments, the first aromatic diepoxy compound comprises at least one N,N-diglycidylaniline group or segment. In some embodiments, the first aromatic diepoxy compound are optionally substituted N,N-diglycidylaniline. The substitutent may be glycidyloxy or N,N-diglycidylanilinyl-methyl. Non-limiting examples of the first aromatic diepoxy compound are N,N-diglycidyl-4-glycidyloxyaniline (DGO) and 4,4'-methylenebis(N,N-diglycidylaniline) (MBD).

The second aliphatic diepoxy compound provides low viscosity and good solubility in an aqueous solution. In some embodiments, the second aliphatic diepoxy compound may be 1,3-butadiene diepoxide, glycidyl ether or $C_{1-5}$ alkane diols of glycidyl ether. Non-limiting examples of the second aliphatic diepoxy compounds are 1,4-butanediol diglycidyl ether (BADGE), 1,2-ethanediol diglycidyl ether, polyglycidyl ether and 1,3-butadiene diepoxide. When the first compound is combined with a second compound, the solubility of the combination in water would increase compared to that of the first compound alone. In some embodiments, the epoxy resin comprises about 10% to about 70%, about 40% to about 60%, or about 50% of the first compound by weight of the epoxy resin, and about 60% to about 40%, about 60% to about 40%, or about 50% of the second compound by weight of the epoxy resin. In some embodiments, the epoxy resin comprises about 50% of N,N-diglycidyl-4-glycidyloxyaniline and about 50% of 1,4-butanediol diglycidyl ether.

In some embodiments, additional compounds may be added to the epoxy resin to improve mechanical properties and chemical resistance. In some embodiments, the epoxy resin further comprises a third compound that is an aromatic epoxy without N,N-diglycidylanaline group. In some embodiments, the third aromatic epoxy compound has at least one glycidyloxy phenyl group,

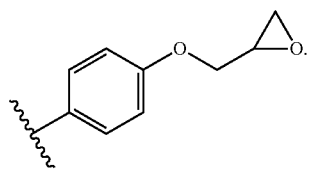 [SMILES: *c1ccc(OCC2CO2)cc1]

In some embodiments, the third compound may be selected from the group consisting of tris(4-hydroxyphenyl) methane triglycidyl ether, bisphenyl-A diglycidyl ether, bisphenyl-F diglycidyl ether and resorcinol diglycidyl ether. In some embodiments, the epoxy resin comprises about 0 to about 25% of the aromatic epoxy without bis-analine group.

In some embodiments, the third compound may be a cycloaliphatic epoxy, and may be 1,4-cyclohexanedimethanol diglycidyl ether or cyclohexene oxide diglycidyl-1,2-cyclohexanedicarboxylate. The cycloaliphatic epoxy may increase the mechanical properties and chemical resistance to a lesser extent than the aromatic epoxy, but with less impact on solubility in water (i.e., does not decrease the overall solubility as much). In some embodiments, the epoxy resin may comprise about 0% to about 50% of the cycloaliphatic epoxy by weight of the epoxy resin.

In yet some other embodiments, the third compound may be an aliphatic epoxy with 3 or more glycidyl ether groups. In some embodiments, the third compound may be polyglycidyl ethers. The aliphatic epoxy with 3 or more glycidyl ether may increase cross linking and thus mechanical properties, but with less impact on solubility.

In general, the solubility of the epoxy resin blend decreases and the viscosity increases as the concentration of the first aromatic diepoxy compound increases. In addition, the mechanical properties and chemical resistance may be reduced as the concentration of the aliphatic diepoxy compound goes up in the epoxy resin blend. By adjusting the ratio of the first aromatic dipoxy compound and the second aliphatic diepoxy compound, a person skilled in the art can control the desired properties of the epoxy resin blend and the hardened media. Adding the third compound in some embodiments may allow further tailoring of the epoxy resin properties.

The hardener comprises at least one cycloaliphatic amine. It provides good combination of reactivity, mechanical properties and chemical resistance. The cycloaliphatic amine may include, but not limited to, isophorone diamine (IPDA), 1,3-bis aminocyclohexane (BAC), diamino cyclohexane (DACH), n-aminoethy pipirazine (AEP), and n-aminopropylpipirazine (APP). The hardener comprises about 75% to about 100% or preferably about 100% of the cycloaliphatic amines as the total amount of amines. In some embodiments, the hardener comprises isophorone diamine (IPDA) and 1,3-bis aminocyclohexane (BAC). The epoxy systems cured by amines do not produce any ester or amide linkages in the backbone that could potentially hydrolyze over time and lead to molecular weight loss, loss in strength or generation of low molecular weight species thus contributing to the stability of the system.

In some embodiments, an aliphatic amine may be added into the cycloaliphatic amine to increase reaction rate, but may decrease mechanical properties and chemical resistance. The preferred aliphatic amine has the structural formula (I):

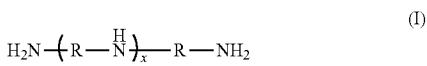

wherein each R is independently selected from branched or linear chains of $C_{2-5}$ alkyl, preferably $C_2$ alkyl, and x is 1-5. The term "alkyl" as used herein refers to a radical of a fully saturated hydrocarbon, including, but not limited to, methyl, ethyl, n-propyl, isopropyl (or i-propyl), n-butyl, isobutyl, tert-butyl (or t-butyl), n-hexyl, and the like. For example, the term "alkyl" as used herein includes radicals of fully saturated hydrocarbons defined by the following general formula $C_nH_{2n+2}$. In some embodiments, the aliphatic amine may include, but not limited to, diethylene triamine (DETA), tri-ethylene tetraamine (TETA), tetraethylenepentamine (TEPA). In some embodiments, the hardener comprises the aliphatic amine at about 0% to about 25% of the total amines.

In some embodiments, the hardener further comprises at least one radio-opaque compound. The radio-opaque compound may be selected from iodo benzoic acids compounds, such as 3,5-diiodosalicylic acid (DSA), 2,3,5-triiodobenzoic acid (TIBA), 3,5-diiodobenzoic acid, iodo benzoic acid, and iodo salicylic acid; aromatic iodo phenol compounds without benzoic acid, such as 4-iodophenol (IP) or 2,4,6-triiodophenol (TIP); aromatic iodine compounds, such as iodobenzene or diiodobenzene; or 3-iodo-1-propanol.

In some embodiments, the iodo benzoic acid compounds have at least one hydroxyl group. In some embodiments, iodo benzoic acid compounds may also catalyze certain epoxy-amine reaction. In some embodiments, the benzoic acid moiety can react with epoxy groups and chemically binds the radio-opaque element to the epoxy. In some embodiments, the hardener comprises the iodo benzoic acid compound at about 5% to about 40%, about 10% to about 30%, about 15% to about 25%, or preferably about 20% by weight of the total amines. In some embodiments, aromatic iodo phenol compounds can be added to provide radio-opacity with moderate catalytic effects. In some embodiments, aromatic iodine phenol compounds may be added to provide radio-opacity with reduced viscosity and no catalytic effect. In some embodiments, either the aromatic iodo phenol compounds or the aromatic iodine compounds is about 5% to about 40% by weight of the total amines.

Some embodiments of the inflation media may also comprise a catalyst to increase the epoxy-amine reaction rate. In some embodiments, the catalyst may be water, benzoic acid based compounds (e.g., poly benzoic acid compounds) or phenol based compounds (e.g., poly phenol compounds). In some embodiments, water may be present at about 0% to about 10%, about 3% to 6%, or preferably about 5% by weight of the total amines. In other embodiments, benzoic acid and phenol based compound may be about 0% to about 40% by weight of the total amines.

The epoxy resin and the hardener in the inflation media disclosed herein can be mixed together to form an epoxy mixture. Each of the two components of the inflation media disclosed herein is typically packaged separately in sterile containers such as syringes until the appropriate time for deploying the device. In some embodiments, the epoxy mixture has an initial viscosity at body temperature of less than about 100 cps, less than about 70 cps, less than about 50 cps, or less than about 30 cps after mixing. In some embodiments, the average viscosity during the first 10 minutes following mixing the two components of the inflation media is about 50 cps to about 60 cps. The low viscosity ensures that the inflation media can be delivered through the inflation lumen of a deployment catheter with small diameter, such as an 18 French catheter.

In some embodiments, the epoxy mixture is soluble in an aqueous environment, such as blood and bodily fluids. In more general terms, it is desirable to use an inflation medium in which each of its components is soluble in blood. A soluble inflation medium is desirable so to manage any embolism risk if released into the vasculature. Such an inflation medium should not gel or solidify if spilled into flowing blood before curing. In the event of a spill, the normal blood flow would then rapidly disperse the components and their concentration would fall below the level required for crosslinking and formation of a gel, semi-solid or solid. These components would then be eliminated by the body through standard pathways without posing an embolic risk to the patient. In some embodiments, a biocompatible inflation medium is desirable so to manage any toxicity risk in the case the inflation medium were inadvertently released into the patient's vasculature.

Once the epoxy mixture is prepared, it can be used to inflate the inflatable structure of a medical device. In some embodiments, the epoxy mixture is formed ex-vivo and delivered to the inflatable structure of a medical device. In some embodiments, the epoxy mixture is delivered via a catheter or delivery lumen to the inflatable device. The epoxy mixture is configured to gel to a semi-solid state or a gel in less than about 4 hours at body temperature (i.e., about 37° C.). In some embodiments, the gel time is about 2 hours to about 4 hours, or about 2 hours to about 3 hours. The gelled epoxy mixture would have a tensile strength of greater than about 20 MPa when it is fully hydrated. The tensile strength measurements were performed on cured epoxy samples immersed in saline for 7 days. In some embodiments, the tensile strength may be from about 20 MPa to about 65 MPa, about 30 MPa to about 65 MPa, about 40 MPa to about 65 MPa, about 45 MPa to about 60 MPa, or about 50 MPa to about 60 MPa.

In some embodiments, the average viscosity of the inflation media at about 37° C. over the first 10 minutes after mixing is less than about 70 cps or approximately 50 cps. An in vitro test for the determination of viscosity is performed by dispensing 0.5 ml of pre-mixed inflation media into a standard cone/plate viscometer that has been stabilized at 37° C. The viscosity is determined in centipoises (cps) from the output on the viscometer. The initial viscosity measurement is taken approximately 30 seconds after mixing is completed. The measurements thereafter are taken about every 3 minutes for approximately 10 minutes. The average measurements are working density. However, in other embodiments, different procedure, implant, delivery system, or inflation media design may require different amount of time for inflation media exchange. It may then be appropriate to calculate the working viscosity over a different period of time such as about 2 min, about 15 min, about 30 min, or about 60 min. In general, a low working viscosity is desirable during the working time.

The working time of the mixed epoxy is defined as the time period during which the viscosity of the inflation media is less than 3 times the viscosity immediately after mixing or the period of time during which the viscosity is less than about 100 cps, less than about 80 cps, less than about 70 cps, or less than about 50 cps. In some embodiments, the working time is when the viscosity of the mixed inflation media is less than about 200, less than about 500, less than about 700, or less than about 1000 cps. A desirable inflation media should have a sufficient working time to complete the exchange of inflation media for the pre-inflation solution.

In some embodiments, the inflation media is fast curing. A fast-curing inflation media allows the implant to achieve and maintain an appropriate stable shape without the risk of leaking or shape changing. By curing quickly, the rigidity of the implant lowers the risk of implant migration and maintains the initial shape. In some embodiments, the inflation media has a low viscosity for the entire working time so that it can be quickly delivered through a small lumen. Then it would quickly reach a solid state with mechanical properties near that of a complete cure.

In some embodiments, the inflation media can achieve much of the benefit by reaching a gel state quickly. In some embodiments, the inflation media reaches a gel state within about 60 minutes, within about 75 minutes, or within about 90 minutes. By gelling within this time period, the risk of any change in the shape of implant after the patient has left the care of the implanting physician is minimized significantly. In some embodiments, the inflation media achieves a viscosity so that it will not cause the implant to loose pressure or leak a significant volume in the event of an implant puncture, shortly after the inflation media is introduced in the implant. When the inflation media has reached such viscosity, only less than about 0.1 ml, less than about 0.05 ml or less than about 0.01 ml of the inflation media is leaked out through a pin hole of about 0.01" to about 0.03" diameter in an inflation channel of about 0.09" to about 0.013" in diameter when the inflation channel is maintained at a constant pressure of about 10 to about 16 atmospheres in about 30 to about 300 minutes. For example, in some embodiments, the risk of significant pressure loss or significant polymer leak due to a small puncture or defect in the inflation channel system of the implant is reduced when the inflation media achieves a viscosity of about 200 to about 2000 cps, or at least about 200 cps in about 5 minutes to about 50 minutes The gel time is determined in vitro by filling inflation lumens with freshly mixed inflation media, curing at 37° C. and cutting the specimens at regular time intervals and assessing the formation of a gel. Inflation lumens with a diameter of about 0.09" to about 0.13" is filled with an inflation media at a suitable pressure between about 10 and about 16 atmospheres. The inflation lumens are immersed in a 37° C. bath. Each inflation lumen is cut at specific time intervals up to about 2.5 hours. At each time interval the inflation lumen is cut and the amount of material that exudes from the cut is visually accessed. When the flow of the inflation media stops or forms a small dome, the material has gelled. In some embodiments, the inflation media forms a semi-solid gel in a range of a few minutes up to about 2.5 hours. In some embodiments, the gel time of the inflation media is less than about 2.5 hours, between about 5 minutes to about 2 hours, about 10 minutes to about 1.5 hours, or about 30 minutes to about 1 hour.

In vitro determination of complete cure and percentage of complete cure can be made by several different methods, including chemical assessment, thermo mechanical assessment, hardness measurement, tensile strength measurement, or other mechanical property measurement. The percentage cure is calculated base on achieving the percentage of the final tensile strength or final hardness of a fully cured polymer. The epoxy reaches a certain percentage cure when achieving that certain percentage of the final tensile strength or final hardness.

The cure time can be determined in vitro via a mechanical cure test, hardness measurements, and a standard tensile test. The mechanical cure test utilizes a three point bend test fixture. An inflation channel is filled with freshly mixed inflation media and the cure time is determined hourly until the inflation channel will elastically support a load in the three point bend configuration. Hardness measurements are done with a hardness tester such a Durometer Gauge. Hardness by this method is measured by the depth of indentation of a needle into the inflation material. The greater the penetration into the curing media, the less cure the curing media is. Once the gage gives the consistent results for each time period from about 10 to about 72 hours, the material may be considered completely cured. In addition, the standard tensile test on non hydrated samples can be made at various time points and compared to data at 7 days to show the stability when compared to tensile properties at later times.

In some embodiments, the inflation media can reach nearly full cure (for example, within about 50 to about 98 percent of the final hardness or tensile strength) and form a solid within about 24 hours. In some embodiments, the inflation media can reach at least about 70% of the complete cure between about 5 to about 48 hours. In some embodiment, the inflation media can achieve a minimum of about 70% cure in less than about 2 hours, less than about 5 hours, less than about 10 hours or less than about 20 hours. In some embodiments, the inflation media can achieve about 95% cure in less than about 100 hours, less than about 80 hours, less than about 50 hours, or less than about 10 hours. Other embodiments achieve at least about 40 to about 95 percent cure in less than about 20 hours, less than about 10 hours, less than about 5 hours, or less than about 2 hours, and at least about 60 to about 99 percent cure in less than about 30 hours, less than about 20 hours, less than about 10 hours, less than about 5 hours, or less than about 3 hours. Some embodiments achieve a tensile strength at maximum load of at least about 7000 to about 12000 psi in less than about 72 hours, less than about 48 hours, or less than about 24 hours.

In some embodiments, the inflation media should exhibit more of elastic material characteristics. The viscoelasticity can be measured using dynamic mechanical analysis (DMA), where an oscillatory force or stress is applied to a material and the resulting displacement or strain is measured. In purely elastic materials the stress and strain occur in phase, so that the response of one occurs simultaneously with the other. In purely viscous materials, there is a phase difference between stress and strain, where strain lags stress by a 90 degree ($\pi/2$ radian) phase lag. Viscoelastic materials exhibit behavior somewhere in between that of purely viscous and purely elastic materials, exhibiting some phase lag in strain. Phase lag ($\delta$) can be calculated as follows:

Strain: $\epsilon = \epsilon_0 \sin(t\omega)$

Stress: $\sigma = \sigma_0 \sin(t\omega + \delta)$ where $\omega$ is period of strain oscillation, t is time, and $\delta$ is phase lag between stress and strain.

The phase lag $\delta$ is used to describe the viscosity of the materials, i.e., a 45° $\delta$ means that the material is half elastic and half viscous. The $\delta$ is studied using DMA and measured as tan $\delta$. Some embodiments provide the inflation media having a phase lag at 1 Hz of less than 5°. Other embodiment have phase lag at 1 Hz of less than about 3, less than about 7, or less than about 10 degrees. Some embodiments exhibit essentially elastic material characteristics with no phase lag.

It is desirable for an inflation media in the cured state to act substantially as an elastic material rather than a viscous material. This allows the implant to better maintain its shape when subjected to continuous cyclic loading. It also facilitates testing the material at accelerated conditions, while maintaining relevance to real time clinical loading conditions. The storage modulus (E') represents the measurement of energy stored during deformation and related to the solid-like or elastic portion of the elastomer for structure support. The loss modulus (E") measures the energy dissipated as heat and represents the viscous portion.

$$\text{Storage: } E' = \frac{\sigma_0}{\varepsilon_0}\cos\delta;$$

$$\text{Loss: } E'' = \frac{\sigma_0}{\varepsilon_0}\sin\delta$$

In some embodiments, the inflation media has storage modulus (E') changes less than about 3%, about 5%, about 10%, about 15%, or about 20% at a frequency of 1, 10, 17, 25 and 32 Hz, respectively, in DMA analysis at 37° C. These frequencies are clinically relevant and are used for accelerated analysis.

In some embodiments, the strain phase lag $\delta$, which represents the viscosity of the viscoelastic material, changes less than approximately 1° between frequencies of 1 Hz and 30 Hz. In other embodiments the change is less than about 0.5, about 2, about 5, or about 7 degrees.

During the curing process, some embodiments of the inflation media go through a more viscous phase. In some embodiments, it is desirable to have an inflation media that is in the viscous phase for a short period of time or where the inflation media still behaves as a relatively elastic material during this phase. One embodiment of the inflation media has a phase lag less than about 50 degrees, less than about 20 degrees, less than about 10 degrees, less than about 5 degrees, less than about 2 degrees, or less than about 1 degree during the entire transition from liquid to solid as tested in a pressurized inflation channel at 37° C. and 1 Hz. Some embodiment of the inflation media have a phase lag greater than about 10, about 15, or about 30 degrees for less than about 150 minutes, less than about 100 minutes, less than about 50 minutes, or less than about 15 minutes as tested under the same conditions.

It is desirable that the inflation media solidifies to form a support structure that is free from significant defects. To prevent bubbles from being trapped in either component of the inflation media, it is preferable that both components have relatively low viscosity prior to mixing. In some embodiments the epoxy component has a viscosity of less than 1000 cps, less than about 500 cps, less than about 200 cps, or less than about 100 cps. It is also desirable that the components do not foam. In some embodiments, each component has a surface tension greater than about 25 dyn/cm. It is desirable that the inflation media expels all of the fluid used to pre-inflate the implant (pre-inflation media) and any trapped bubbles. Thus, the inflation media and the pre-inflation solution should have similar densities. In some embodiments, both inflation media and pre-inflation solution have a density of approximately 1.11 g/ml. In some embodiments, the density is between about 1 and about 1.3 g/ml. In some embodiments, the density difference of the two solutions is less than about 10%, less than about 5%, or less than about 1%. The inflation media and pre-inflation solution preferably are designed such that when 1 excess volume of inflation media has been exchanged through the implant, about 99 to about 99.9% of the pre-inflation solution has been displaced.

Polymers, such as some embodiments of cured inflation media, can deform over time with a constant load, which is referred to as creep. Because the inflation media will form the structural frame of the implant, any change in dimension as a result of creep should be minimal and not affect the performance of the device. The strain induced from the creep can be referenced back to the Finite Element Analysis to determine the change in the implant dimensions.

Creep

Creep has been an important factor in prosthetic heart valves with polymer support structures. Some surgical designs have deformed over time sufficiently to reduce the amount of blood flow through the valve. Some embodiments provide a prosthesis that is designed to significantly reduce the stresses in the polymer filled support structure, to less than about 0.5 MPa. In other embodiments, the stress was reduced to less than about 10 MPa, less than about 5 MPa, or less than about 1 MPa. This could be done by connecting the commissural supports with a ring on the outflow side of the prosthesis as disclosed in U.S. Pat. No. 7,445,630, and further providing in interference fit between the inflation channels within the aortic ring and the fabric covering surrounding the inflation channels such that the loads are transferred between the sections of polymer that are separated by the inflation channel.

In some embodiments, it is desirable that the substantially cured inflation media exhibit less than about 10% creep, less than about 5% creep, less than about 2% creep, less than about 1.5% creep, or less than about 1% creep in 10 years, at clinically relevant loading conditions or at about 0.5 MPa, both in real time and in predicted creep life determined in the method described below.

A creep mold is filled with the following mixed two-part inflation media (IM-A) to make a creep sample with a thickness of about 2 mm and a width of about 4 mm.

Part A: 50% N,N diglycidyl-4-glycidyloxyaniline (DGO) and 50% 1,4 butanediol diglycidyl ether (BADGE)

Part B: isophorone diamine (IPDA) and 1,3 bis(aminomethyl cyclohexane (BAC)

The creep sample was cured in an incubator at 37° C. for a minimum of 24 hours, and then placed in a 37° C. saline solution for 7 days to simulate hydration in a clinical setting. Removed the creep samples from the saline and deburr any flash and break sharp edges. Dried the surface of each sample and measured the width and thickness. Placed the samples in a flexural creep test stand as described in ASTM D 2990 with the samples submerged in water. This provides a span of 2 inches on the creep sample when placed in a three point bend fixture. Once the samples were loaded in the fixture the dial gauge was set to zero for all samples. The amount of weight to be added to the fixture was calculated to apply the desired stress on each sample. The amount of deflection for all samples were initially measured at various time intervals up to 1, 2, or 3 years, to create a curve. The curve can be extrapolated once it has become relatively linear.

In some embodiments, the inflation media will exhibit a maximum strain of less than 1% at 60 days when a load of 1.5 MPa is applied. Other embodiments of the inflation media exhibit less than 5% maximum strain due to creep under the same loading and time conditions. Some embodiments exhibit a maximum of about 5% to about 15% strain due to creep when a load of 10 MPa is applied under the same loading and time conditions. None of the commercially available polymers evaluated met the criteria above even at stress levels reduced by at least an order of magnitude.

Rotating Beam Fatigue Testing

The inflation media is subjected to a cyclical load as a result of the hemodynamic forces applied to the valve. The fatigue properties can be evaluated by using rotating beam test configuration. In rotating beam testing the test sample is loaded as a cantilever beam and rotated creating an alternating stress throughout its circumference. The data is plotted as the max cyclical stress (S) as a function of the number of cycles (N). This is known as the S-N curve. S-N data generated from rotating beam can be applied conservatively to clinical loading. Because the stress levels will pass through the full tensile and compressive load, it can be applied conservatively to clinical load values.

Figure 4:
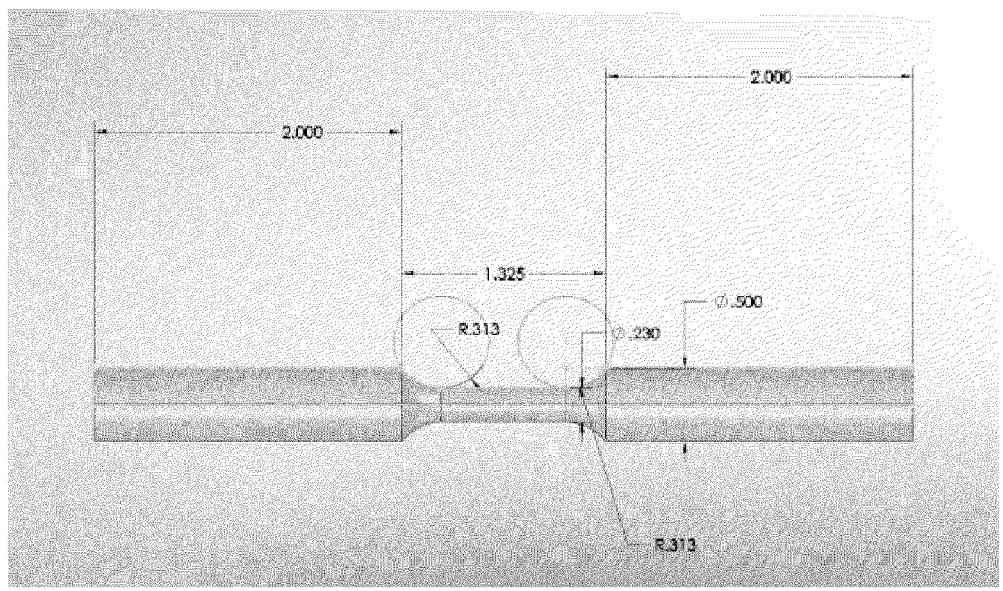
FIG. 4 shows a rotating beam test specimen.

Rotating beam fatigue testing is performed per standard practice using a reduced cross section sample of the dimensions shown in FIG. 4. The samples are cooled during cure to ensure the polymer does not see an elevated temperature greater than 42° C., which could result in slightly different mechanical properties. After curing, the samples are hydrated by submerging in saline solution for two weeks (14 days) before rotating beam fatigue testing is started. Rotating beam fatigue testing is performed per industry standard and submerged in water or saline solutions.

In some embodiments, the inflation media may have a fatigue life longer than about 600 million cycles, or 15 patient years when loaded at 1.5 MPa, as predicted by the S-N curve. In some embodiments, at least 50% of samples tested at 15 MPa survive at least about 300 million cycles. In other embodiments at least 50% of samples tested at 2 to 20 MPa survive at least about 100 million cycles, at least about 50 million cycles, or at least about 10 million cycles. In other embodiments, the S-N curve will predict a fatigue life of at least about 1000 million cycles, at least about 500 million cycles, or at least about 100 million cycles when loaded at 1.0 to 15 MPa.

Tensile Testing

Tensile Testing is a fundamental mechanical test useful in obtaining strength information about a material. Using a constant cross head speed and a strain gauge also referred to as an extensometer, the Modulus of Elasticity (Young's Modulus), the Tensile stress at maximum load, tensile strain at maximum load, and the tensile strain at break can be determined.

Tensile specimens are prepared by filling a dogbone shaped tensile mold with approximately 10 grams of mixed 2-part-inflation media. Dogbone shape is standard for tensile testing based on ASTM 638 shape, scaled to provide a cross sectional thickness representative of the implant geometry. The tensile sample is allowed to cure at ambient conditions overnight and then cure in an incubator at 37° C. for a minimum of 24 hours. Remove the tensile specimens from the molds and place in a labeled container filled with 0.9% saline at 37° C. Store the samples at this temperature for the desired length of time before testing. Remove samples from the storage container and remove any flash while breaking any sharp edges. Using calibrated calipers, find the smallest values of thickness in the gauge area of the sample and record the results. Measure and record the width of each sample. Place samples in a 37° C. bath near the Instron (tensiometer). Turn on power to a heater on the tensiometer and stabilize the environment around the grips at 37° C. Connect the appropriate load cell on the tensiometer. Calibrate the tensiometer and balance the load cell. Attach an extensometer to the tensiometer. Testing is performed at a cross head speed of 1.00 in/min and data capture rate of 50 ms. Load the specimens into the grips and attach the extensometer to the tensile specimen. Balance the strain gauge and start the test.

In some embodiments of the inflation media, the tensile stress at maximum load is greater than 1.5 MPa. In other embodiments the tensile stress at maximum load is greater than about 5 to about 50 MPa at 37° C. when determined by testing on a tensiometer.

Some embodiments of the cured inflation media have a Young's Modulus of approximately 2500 MPa, a tensile strain at maximum load of approximately 3.5% and a tensile strain at break of approximately 3.9% when modified dogbone samples are tested. Similar results are obtained with slightly lower elongation when tested in inflation channels.

Other embodiments have a Young's Modulus of approximately 500 MPa to approximately 5000 MPa, a tensile strain at maximum load of approximately 1% to approximately 10% and a tensile strain at break of approximately 1% to approximately 10% when modified dogbone samples are tested. Similar results are obtained with slightly lower elongation when tested in inflation channels.

Some embodiments have a tensile stress at maximum load in the range of about 25 to about 150 MPa over a time period of 24 hours to 5 years when tested at 37° C. on a tensiometer. Some embodiments will have a Young's Modulus ranging from about 1,000 to about 10,000 MPa, and a tensile strain at maximum load as well as tensile strain at break in the range of about 1% to about 20% in 24 hours to 5 years.

Inflation Media Safety

It is also desirable that releasing of a small amount of the inflation media into the blood stream does not result in clinically significant embolic events. For example, when the inflation media is spilled into the blood stream, it should disperse, dissolve, or not create particles larger than about 10 µm. Studies by A. Colombo, et al. have determined that large particles (>100 µm) may obstruct large, epicardial vessels and very small particles, as little as 15-50 µm, can also obstruct the microvascular bed causing microinfarcts and left ventricular dysfunction.

In some embodiments, an inflation media has a low viscosity of about 10 to about 70 cps in the first 1 to 10 minutes after initial mixing. Blood soluble materials with high viscosities may not disperse quickly in blood. Lower viscosity water-soluble materials are more tolerated in blood than higher viscosity water-insoluble materials. In some embodiments, the inflation media is capable of being injected via catheter in the aorta or left ventricle in an amount of about 0.2 to about 20 ml without causing a major clinical event as seen by significant EKG change, Cardiac enzyme changes CK, CK-Mb Troponin (ranges), pathological and histological examination of tissues, and major organs (heart, kidneys, liver, spleen, lungs, and brain).

In Vivo Spill Study

In vivo testing via a Spill Study is performed to demonstrate the tolerance of an inadvertent release of the inflation media into the blood stream. Literature has demonstrated this animal model to be a good foundation for preclinical analysis. Animals were anesthetized, prepared for sterile surgery and access to the femoral artery obtained. Blood pressure and heart rate are monitored during the procedure. A baseline EKG and blood sample are obtained. A catheter is placed in the area of sinus of valsalva and 0.6 ml to 3.0 ml of inflation media is injected into the ascending aorta. 0.6 ml corresponds to an amount more than the volume of the aortic ring and significantly more than the volume released in a simulated rupture. Larger volumes were evaluated for conservatism and to characterize the volume effect of the response. After injection, angiography of the coronary arteries and aortic arch are made, and EKG is recorded at 1, 10, 20, and 30 minutes. Blood samples are taken 30 minutes after injection, once the animal has recovered form anesthesia, 12 hours post-procedure, and on post-procedure days 2, 3, 7, 14, and 30. Animals are euthanized and major organs observed grossly and sent for histopathological evaluation. With a 0.6 to 0.75 ml injection of inflation media, the animals survive and show no signs of organ failure during the 30 day evaluation period as a result of the injection of the inflation media IM-A (as described above). The animals do not show neurological impairment and no evidence of inflation media or its components are found at histopathology. The EKG may show minor non-specific transient changes that are typical for the animal model, but does not show signs of a major ischemic event. Blood pressure may reduce slightly at the time of injection but returns to within at least 80% of baseline within 30 minutes. The rises in CK, CKmb, and troponin enzymes are similar to control animals with similar catheter manipulation but without inflation media injection.

Solubility of Inflation Media

In some embodiments, the inflation media is also soluble in water or saline. The inflation media IM-A is placed in a centrifuge tube with phosphate buffered saline in a ratio of one part inflation media to nine parts saline. The solution is thoroughly agitated and then spun in a centrifuge. The result showed that at least about 99%, at least about 90%, at least about 80%, or at least about 50% of the inflation media is dissolved in the water with the remaining portions visible or detectable above or below the dissolved portion.

The solubility of the inflation media can also be tested by diluting 0.1 ml of inflation media in 9.9 ml water and mixing in a vortex mixer at 3000 rpm for 30 seconds to form an inflation media solution. A 20 c.c. syringe with dessicated 0.2 micron syring filter attached was used to draw the mixture through the syringe filter. The syringe filter was dried thoroughly, and the residue in the filter was weighed. In some embodiments, the inflation media solution leaves behind less than 0.3 g or less than 0.1 g of residue.

Heat Generation During Curing

For some embodiments, it is desirable that the inflation media cure in the body without generating excess heat or causing a temperature at the surface of the implant to be greater than 40° C. or greater than 42° C. Temperatures above these can cause cell death, changes to extracellular matrix or other adverse biologic reactions. The cure time testing is performed in vitro using dual thermocouples. One thermocouple measures the temperature of the circulating 37° C. physiological solution and the other is placed directly inside the inflation media filled channel. The temperature is monitored until the inflation media cures and the highest temperature is reported. Alternatively the thermocouple can be placed on the surface of the inflation channel and held in contact by a fabric sleeve with an interference fit.

pH Change Due to Spill

It is desirable for the pH of the inflation media to change no more than 0.4 pH point from a baseline of 7.4 pH. Increased pH can cause heat/burn trauma to tissue and blood, resulting in adverse hemostatic events leading to embolic events. In this test the volumes have been scaled from a human blood volume and worst case spill volume to 0.1 ml of mixed media into 783 ml of phosphate buffered saline. The solution is measured using a pH meter. The inflation media IM-A does not raise the pH in this scaled solution more than about 0.2 at 25° C. In some embodiments, the spilling of inflation media in the body does not raise the pH more than about 0.1, about 0.2, about 0.4, about 0.6, and about 1.0 pH unit when a clinically relevant amount (e.g., about 0.4 ml to about 0.8 ml) is spilled.

Tg

In some embodiments, the inflation media has a glass transition temperature (Tg) that is above human body temperature ranges. In some embodiments, the inflation media has a Tg of greater than about 50° C. as measured by DSC and DMA. Other embodiments have Tg greater than about 37° C., about 40° C., about 60° C., or about 90° C. as measured by DSC and DMA. In some embodiments, the inflation media does not have a phase transition, transition temperature or inflection point in thermal mechanical properties at about 36° C. to about 38° C. or in the range of about 34° C. to about 42° C. Some embodiment do not have a phase transition, transition temperature or inflection point in thermal mechanical properties at about 10° C. to about 60° C. or about −20° C. to about 100° C.

Differential scanning calorimetry (DSC) is thermoanalytical technique that measures the changes in the heat flow rate between a sample and a reference subjected in a controlled temperature program. The main application of DSC is studying phase transitions, such as melting, glass transitions, or exothermic decompositions. These transitions involve energy changes or heat capacity changes that can be detected by DSC with great sensitivity. The DSC is performed with dry cured samples.

Figure 5A:
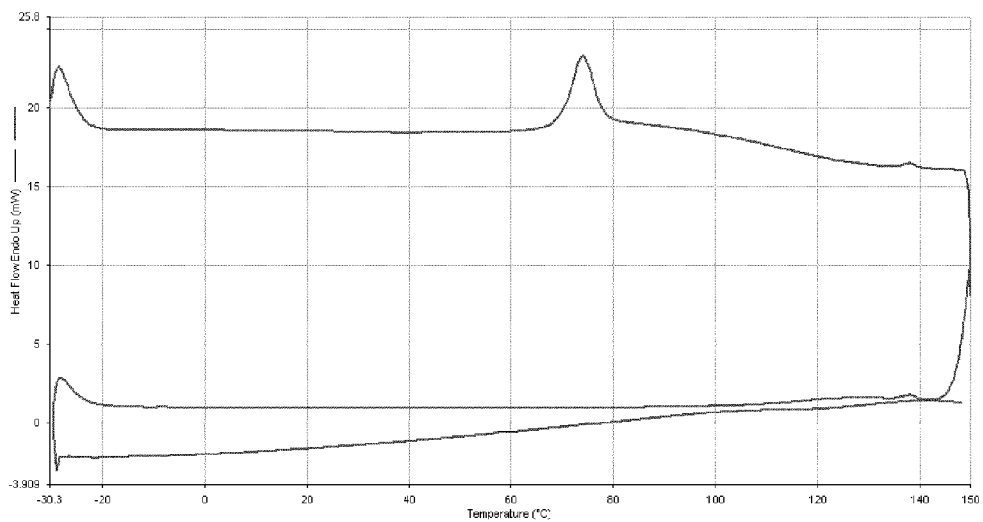
FIGS. 5A and 5B is a plot of heat flow as a function of temperature in the differential scanning calorimetry (DSC) measurements.
Figure 5B:
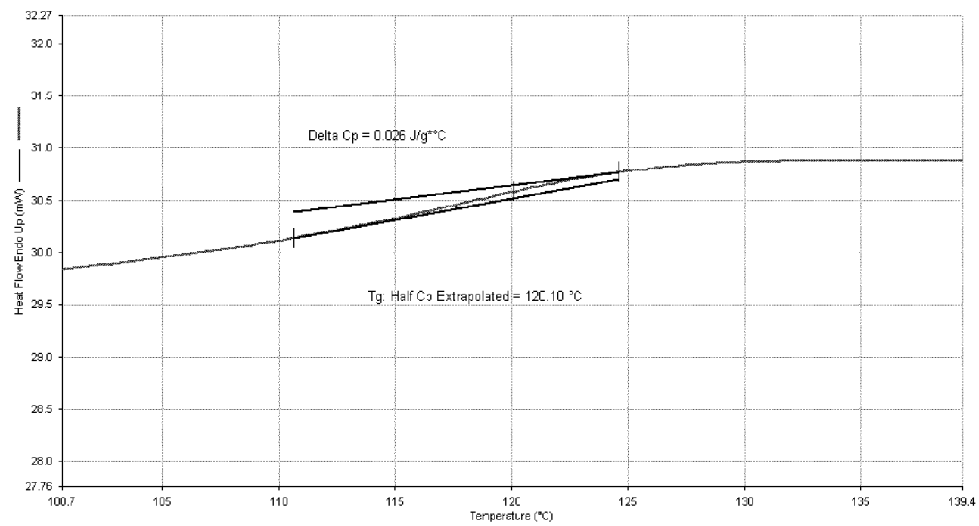

One drop of the mixed inflation media IM-A is placed into a DSC pan. Repeat this step so that the required number of DSC samples is assembled. Put the samples on a weigh boat and place them in a 37° C. (±3° C.) incubator/oven for 12 to 24 h. Remove the pans from the incubator and place one sample pan into a solid crimper press. Cover the pan with sample lid and crimp until pan is sealed. Start the gas flow and place the samples in the DSC. Set the DSC to scan from −30° C. to 150° C. at 20° C./min and collect data at appropriate intervals, at least 500 points. Plot heat flow as a function of temperature (see FIGS. 5A and B) and analyze the resulting curve.

Dynamic Mechanical Analysis (DMA) is a technique where a small deformation is applied to a sample in a cyclic manner. This allows the materials response with regards to stress, temperature, frequency and other values to be studied. Dynamic Mechanical Analysis measures the mechanical properties of materials (modulus) as a function of time, temperature, and frequency. DMA is most often used in polymer analysis to measure the change in modulus as a function of temperature and hence the glass transition temperature. DMA can be run with dry and saline aged samples.

The DMA samples are cylindrical samples of approximately 2 to 3 mm diameter and the length of the span is set to 20 mm. The temperature ramp rate is set to 4° C./min and sampling rate to 3 sec. The frequency is set to sinusoidal oscillation mode at 1 Hz. For 1M-A, a 20 micron amplitude is appropriate. Elastic modulus is plotted as a function of temperature. The resulting curve shows an inflection point at temperatures where there is a thermal transition. The thermal transition occurs at about 64° C., which is much higher than the body temperature.

Leachable Analysis

The preferred embodiments of the inflation media do not leach significant amounts of any chemical in physiological solutions. Additionally, the preferred embodiments of the inflation media do not leach significant quantities of chemicals in strong polar and non-polar solvents, indicating that the polymer is stable. 1 ml of inflation media is cured at 37° C. for 24 hours to form a sample with a clinically relevant cross sectional diameter of 2-3 mm. The sample is placed in a 20 ml solution of phosphate buffered saline, hexane, or methanol for 3, 7, 14, and 30 days. The solutions were analyzed by gas chromatography-mass spectrometry (GC-MS) and inductively coupled plasma mass spectrometry (ICP-MS). In some embodiments, the solutions were found to contain less than about 10 ppm, less than about 1 ppm, less than about 0.1 ppm, or less than about 0.01 ppm of any component or reaction product of the inflation media at any one of the testing intervals 3, 7, 14, and 30 days.

Leachable analysis can also be performed to monitor the progress of the curing process and evaluate the stability of a polymer over time. The lack of long term leachables is usually indicative of completion of the curing process to form a stable polymer system. In a typical polymer system, leachates usually occur during the initial curing phase, and during post cure secondary stabilization phase. During the initial phase of curing in a polymer system, several unreacted compounds may elute from the curing system. Once the polymer reaches full cure, leachates should be greatly reduced. As a polymer system ages and undergoes post-cure secondary stabilization during aging, this change in conformation may also release some trapped leachates. Once this stabilization is complete, the leachates should again fall to a minimum. An indication that a complete cure has been achieved is minimal amounts of epoxy or amine being extractable from the cured polymer, even in strong solvents. In some embodiments, the inflation media reach a state of complete cure at body temperature (i.e., about 37° C.) without requiring an elevated temperature as many epoxy systems may require.

Biocompatibility

In some embodiments, the inflation media should have minimal to no effect on the biological system in the potential spill volumes. For examples, the inflation media does not have a significant vasodilation effect that some amines are known to possess. The preferred embodiment of the inflation media will not cause a reduction in diastolic blood pressure of more than about 5% about 10%, or about 20% as measured about 5 to about 60 mins after the delivery of 3 ml of inflation media over 30 sec. in the descending aorta of a 50 kg sheep. The inflation media also does not have a significant cardiac depressant effect. About 1.5 ml of inflation media delivered over 15 sec. into the left ventricle of a 50 Kg sheep will not cause a reduction is systolic blood pressure greater than about 5%, greater than about 10%, or greater than about 20% when measured 1 to 30 minutes after injection.

In some embodiments, the inflation media do not cause the activation or aggregation of platelets as compared to a control. Test samples of inflation media are prepared by mixing the inflation media and filling a sample implant or inflation channel portion of the implant. The sample is then cured in about 37° C. saline solution and extracted using MEM solution per ISO 10993-5 standard method for cytotoxicity testing. When tested per USP 30<87> MEM Elution, or per ISO 10993-5, the results indicated less than grade 1 cell lysis, less than grade 2 cell lysis, or less than grade 3 cell lysis. When tested in accordance with United States Pharmacopeia USP 30 (2007), Section 88, Biological Reactivity Test In Vivo, Systemic Injection Test and, ISO 10993-11: 2006 Biological Evaluation of Medical Devices Part II: Tests for Systemic Toxicity, the inflation media exhibits less than 5% hemolysis. When tested in accordance with ASTM Hemolysis Assay, Direct Contact Method, extracting in a ratio of 5 g/10 ml in phosphate buffered saline for three hours at 37° C., the inflation media also exhibits less than 5% hemolysis. The blood used in the assay was checked to see the plasma free hemoglobin value.

In some embodiments, the inflation media should be a non-irritant. Dermal score of <1 and an irritant ranking score of about 2.9 or less are desired when evaluated per:

(1) ISO 10993-10:2002 Biological Evaluation of Medical Devices. Part 10: Tests for Irritation and Delayed-type Hypersensitivity, and (2) Intracutaneous Reactivity Test. USP 30 <88>, Biological Reactivity Tests, In Vivo Implantation Test.

In some embodiments, the inflation media is a non-sensitizer. The Stimulation index should be <3.0 when tested per ISO 10993-10:2002 Biological Evaluation of Medical Devices. Part 10: Tests for Irritation and Delayed-type Hypersensitivity.

In some embodiments, the inflation media is non-mutagenic when tested in accordance With AS TM F2148-07 and ISO 10993-10:2003 Biological Evaluation of Medical Devices. Part 3: Tests for Genotoxicity, Carcinogenicity and Reproductive Toxicity.

Stability

In some embodiments, the inflation media does not form any precipitates when stored at a temperatures ranging from about 0° C. to about 30° C. or from about −20° C. to about 50° C. In some embodiments, the inflation media has a shelf life of about 5 years before sterilization and about 1 year after sterilization. Some embodiments have shelf lives of about 2 to about 5 years after sterilization. Other embodiments have shelf lives of at least about 1 month, at least about 3 months, or at least about 6 months after sterilization.

In some embodiments, the inflation media is clear. Other embodiments have a yellow tint. This color helps to distinguish the inflation media from other non-solidifying solutions used in the cardiac catheterization lab. Some embodiments provide an inflation media, in the unmixed state, having both components appear transparent or translucent. This allows easy inspection for particulate and can provide a positive perception of the customer. Previous radio opaque systems developed to solidify in the body have been opaque, translucent or cloudy. The preferred embodiment when tested per ASTM D-1003 (Standard Test Method for Haze and Luminous Transmittance of Transparent Plastics) has a light transmission percentage between 40% and 90%. Other embodiments have a light transmission percentage over 85%.

In some embodiments, the inflation media has a mild odor allowing it to be distinguished from other fluids in the catheter lab and allowing detection of a leak or spill on the table, which might be treated differently from a spill within the patients blood stream. The odor is not unpleasant or overwhelming, as is possible with some amine selections. During the normal procedure at a distance of 24 inches, a simplified odor meter should detect less than about 5, less than about 10, or less than about 50 ppm from the amine component. During a leak of 0.2 ml of inflation media on the bench in a similar test setup the instrument should detect approximately 0.1 to approximately 1 ppm of the amine component. In some embodiments, with other amine formulations, the instruments should detect about 1 to about 10 ppm, or about 10 to about 100 ppm.

In some embodiments, the inflation media does not swell significantly when placed in an aqueous environment such as the body. This can prevent excessive dimensional change during the life time. In some embodiments, a slight degree of swelling may be desirable to effectively increase the pressure between the prosthesis and the body.

Some embodiments provide an inflation media that does not absorb excessive amounts of water over time, when submerged in physiological fluids or saline solution. It absorbs less than about 10% of its original weight in water at 90 days, and less than about 7% at 30 days when tested in a 2 to 3 mm cross section. In some embodiments, by the $20^{th}$ day, the inflation media has absorbed half of the amount of water it will absorb in 90 days.

In some embodiments, the cross-sectional diameter change due to water absorption of the cured inflation media is less than about 1% at 90 days, and at least about 50% of the increase in diameter has been achieved by 10 days. Tests are performed on samples with a cross-sectional diameter between 2 and 3 mm. Some tests are performed inside the inflation channel of the prosthesis and some are performed with the inflation media alone. The specimens are removed and the surface dried for measurement. The results between the test set ups are very similar. The samples are immersed and stored in 37° C. phosphate buffered saline solution.

Pre-Inflation Media

In some embodiments, the balloon or inflation channel may be connected to the catheter on both ends. This allows the balloon to be pre-inflated with a non-solidifying material such as a gas or liquid. In some embodiments, a gas pre-inflation media may be $CO_2$ or helium. These gases may also be used to inflate intraortic balloon pumps. In some embodiments, the pre-inflation media is radio-opaque so that the balloon or the implant position can be determined by angiography. Contrast media typically used in interventional cardiology could be used to add sufficient radio-opacity to most liquid pre-inflation media.

In some embodiments, liquid pre-inflation media may comprise a commercially available contrast solution intended for intravascular injection (for imaging purposes). In some embodiments, the contrast solution is diluted with at least one of sterile saline, a low density component, and a buffer. The contrast solution comprises an iodine component. In some embodiments, the iodine component is an organically-bound iodine. Examples of the iodine component include, but not limit to, sodium diatrizoate (NaDTA), iodixanol, etc. The low density component may be a liquid with a specific gravity less than about 0.99, less than about 0.9, or less than about 0.8. Some examples of the low density component include, but not limit to, ethanol, methanol, polyethylene glycol (PEG), etc. The buffer may be a phosphate buffer, such as a phosphate buffer saline, HEPES, TAPSO, TES, MOPS, SSC, etc. In some embodiments, the pre-inflation media comprises contrast solution, water, and a low density component. In some embodiments, the pre-inflation media further comprises a buffer and/or sodium chloride. In one embodiment, the pre-inflation media comprises an organically bound iodine, water, ethanol, and optionally a phosphate buffer and/or optionally sodium chloride.

The ingredients of the pre-inflation media are mixed in a ratio to achieve the desired radio-opacity and a density that matches the density of the inflation media. The density balance is desirable because it allows the inflation media to expel nearly all of the initial inflation solution without flushing excess volumes of inflation media through the system. If the pre-inflation media is significantly more dense than the inflation media pockets of pre-inflation solution tend to form in the areas of the implant that were lowest during the exchange and cure process. If the pre-inflation media is significantly less dense than the inflation media pockets of pre-inflation solution tend to form in the areas of the implant that were highest during the exchange and cure process. Some embodiments of the pre-inflation solution are packaged ready to use in a sterile container. Other embodiments are mixed in the clinical setting.

When it is desired to make the implant permanent and exchange the pre-inflation media for the permanent inflation media, the permanent inflation media is injected into the inflation channel through a first catheter connection. In some embodiments, the permanent inflation media is capable of solidifying into a semi-solid, gel or solid state. As the permanent inflation media is introduced into the inflatable structure, the pre-inflation media is expelled out from a second catheter connection. The catheter connections are positioned in such a way that substantially all of the pre-inflation media is expelled as the permanent inflation media is introduced. In one embodiment an intermediate inflation media is used to prevent entrapment of pre-inflation media in the permanent inflation media. In one embodiment the intermediate inflation media is a gas and the pre-inflation media is a liquid. In another embodiment the intermediate inflation media or pre-inflation media functions as a primer to aid the permanent inflation media to bond to the inner surface of the inflation channel. In another embodiment the pre-inflation media or the intermediate inflation media serves as a release agent to prevent the permanent inflation media from bonding to the inner surface of the inflation channel. In some embodiments, the inflation media exchange may be performed at a pressure range of about 8 atm to about 20 atm, about 10 atm to about 18 atm, or about 12 atm to about 16 atm.

Radiopacity

In some embodiments, the radiopacity of the inflation media and the pre-inflation media may allow physicians to identify the structural frame of the implant under fluoroscopic examination. Radiopacity is created in the inflation media system by adding a radiopaque additive to the amine portion of the inflation media. When mixed with the epoxy portion, the resulting product will become radiopaque under fluoroscopic examination. The pre-inflation media is a density balanced contrast system to be used with the inflation media. In some embodiments, iodine is used to add the radiopacity.

The radiopacity for medical use can be determined by one of the three industry standards:

Method A—Radiopacity is (1) qualitatively determined by viewing image(s) of a test sample and the image background, with or without the use of a body mimic, or (2) quantitatively determined as a specific difference in optical density or pixel intensity between the image of a test sample and the image background, with or without the use of a body mimic.

Method B—Radiopacity is determined by (1) qualitatively comparing image(s) of a test sample and a user-defined standard without the use of a body mimic, or (2) quantitatively determining the specific difference in optical density or pixel intensity between the image of a test sample and the image of a user-defined standard without the use of a body mimic.

Method C—Radiopacity is determined by (1) qualitatively comparing image(s) of a test sample and a user-defined standard with the use of body mimic or (2) quantitatively determining the specific difference in optical density or pixel intensity between the image of a test sample and the image of a user-defined standard with the use of a body mimic.

The permanent inflation media may have a different radio-opacity than the pre-inflation media. A device that is excessively radio-opaque tends to obscure other nearby features under angiography. During the pre-inflation step it may be desirable to visualize the inflation channel clearly, so a very radio-opaque pre-inflation media may be chosen. In some embodiments, the pre-inflation media has at least about 5, at least about 10, at least about 25, or at least about 35 g/ml iodine. In some embodiments, the pre-inflation media has about 18 g/ml iodine. After the device is inflated with the permanent inflation media, a less radio-opaque inflation media may be preferred. In some embodiments, the inflation media has about 3 to about 5 g/ml iodine. Other embodiments have at least about 3, at least about 5, at least about 10, or at least about 20 g/ml iodine. It is further desirable that the implant maintain radiopacity after the exchange is complete so that the physician can visualize any change in location of the implant immediately after the procedure and as a follow-up for future fluoroscopic evaluations. The feature of lesser radio-opacity is beneficial for visualization of proper valve function as contrast media is injected into the ventricle or the aorta. In some embodiments, it is also desirable to have a visible gradient of radiopacity between the pre-inflation media and the inflation media, making the completion of the exchange more definitive.

Sterilization

The inflation media and the pre-inflation media can be sterilized by radiation without breaking down or reducing the shelf life to an unacceptable level. Sterilization may be done by Electron beam sterilization method at a dose of 10, 15, or 25 Kilogray. Some embodiments of the inflation media are self sterilizing. Some embodiments are bacteriostatic. Some embodiments of the inflation media or the pre-inflation media must be sterilized by sterile filtration methods. Some embodiments may be sterilized by heat such as autoclave. In some embodiments, the inflation media or the pre-inflation media is chilled to less than −10, 0, or 25'C before it is placed in the radiation sterilization chamber. In some embodiments, the inflation media or the pre-inflation media is sterilized in multiple radiation cycles.

Delivery Catheter

FIGS. 6-9 illustrate an embodiment of a delivery catheter 300 that can be used to deliver the valve 100 describe above. In general, the delivery catheter 300 can be constructed with extruded tubing using well known techniques in the industry. In some embodiments, the catheter 300 can incorporates braided or coiled wires and or ribbons into the tubing for providing stiffness and rotational torqueability. Stiffening wires may number between 1 and 64. More preferably, a braided configuration is used that comprises between 8 and 32 wires or ribbon. If wires are used the diameter can range from about 0.0005 inches to about 0.0070 inches. If a ribbon is used the thickness is preferably less than the width, and ribbon thicknesses may range from about 0.0005 inches to about 0.0070 inches while the widths may range from about 0.0010 inches to about 0.0100 inches. In another embodiment, a coil is used as a stiffening member. The coil can comprise between 1 and 8 wires or ribbons that are wrapped around the circumference of the tube and embedded into the tube. The wires may be wound so that they are parallel to one another and in the curved plane of the surface of the tube, or multiple wires may be wrapped in opposing directions in separate layers. The dimensions of the wires or ribbons used for a coil can be similar to the dimensions used for a braid.

Figure 6:
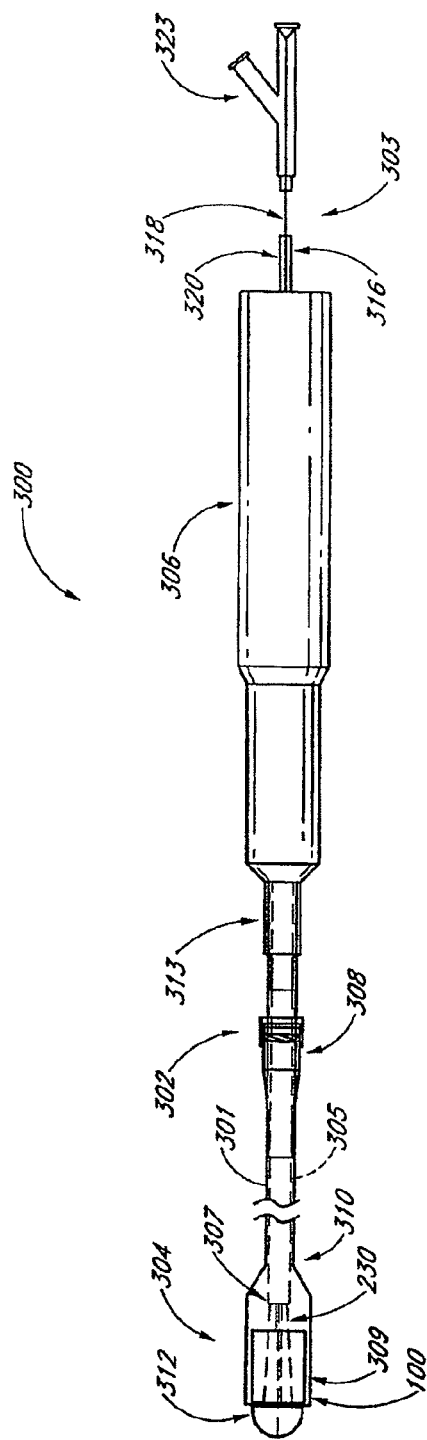
FIG. 6 is a side view of a deployment catheter.

With initial reference to FIG. 6, the catheter 300 generally comprises an outer tubular member 301 having a proximal end 302 and distal end 304 and an inner tubular member 305 also having a proximal end 303 and a distal end 307. The inner tubular member 305 extends generally through the outer tubular member 301, such that the proximal and distal ends 303, 307 of the inner tubular member 305 extend generally past the proximal end and distal ends 302, 304 of the outer tubular member 301. The proximal end 303 of the inner tubular member 305 includes a connection hub or handle 306 to mate other lab tools and to grasp and move the inner member 305 with respect to the outer member. A hemostasis valve 308 is preferably provided between the inner and outer members 301, 305 at the proximal end 302 of the outer tubular member 301. A strain relief 313 is preferably provided between the inner tubular member 305 and the handle 306 to limit strain on the inner member 305. The proximal end 302 of the outer tubular member 301 can include a grasping member or handle (not shown) for holding the outer tubular member 301 stationary with respect to the inner tubular member 305.

In one embodiment, the outer diameter of the catheter 300 measures generally about 0.030 inches to 0.200 inches with a wall thickness of the outer tubular member 301 being about 0.005 inches to about 0.060 inches. In another embodiment, the outer diameter ranges from about 0.15 inches to about 0.35 inches or from about 12 French to about 27 French. In this embodiment, the wall thickness of the outer tube 301 is between about 0.005 inches and about 0.030 inches. The overall length of the catheter 300 ranges from about 80 centimeters to about 320 centimeters.

As mentioned above, the catheter 300 includes a connection hub or handle 306 that is configured to allow wires, devices and fluid to pass as will be explained in more detail below. The connection hub 306 is preferably compatible with normal cath-lab components and can utilize a threaded end and a taper fit to maintain seal integrity. The inner diameter of the inner member 305 of the catheter 300 is configured allow for coaxial use to pass items such as guidewires, devices, contrast and other catheters. An inner lining material such as Teflon may be used to reduce friction and improve performance in tortuous curves. Additionally, slippery coatings such as DOW 360, MDX silicone or a hydrophilic coating from BSI Corporation may be added to provide another form of friction reducing elements.

Multidurometer materials in the catheter 300 can help to soften the transition zones and add correct stiffness for pushability. Transition zones may also be achieved through an extrusion process know as bump tubing, where the material inner and outer diameter change during the extrusion process. The entire catheter shafts 301, 305 can be produced in one piece. Another method for producing such a catheter shaft is to bond separate pieces of tubing together by melting or gluing the two components together and forming a single tube with multiple diameters and or stiffness. The application of heat can be applied by laser or heated air that flows over the shaft material or other methods of heat application sufficient to flow the materials together.

With continued reference to FIG. 6, the distal end 304 of the outer sheath 301 comprises an enlarged diameter section 309, which is configured to cover the implant 100. In one embodiment, the diameter of the enlarged diameter section 309 where the implant 100 is contained is between about 0.20 inches and about 0.32 inches in diameter with a length between about 0.5 in and about 5.0 inches. A second portion 310 of reduced diameter and increased flexibility is located proximal to the section 309 that covers the implant 100. This section ranges from about 0.10 inches to about 0.25 inches in diameter. In the preferred embodiment, the distal section 309 is about 0.29 inches diameter, and about 0.08 inches in length and the proximal section 310 has an outside diameter of about 0.19 inches. The enlarged distal portion 309 can be made from a material with a higher durometer than the proximal portion 310 of the catheter 300. In one embodiment, the material of the enlarged distal portion 309 is a biocompatible material. In another embodiment, the material is a metallic material such as stainless steel. In another embodiment, the material is a polymer such as FEP, PEEK or a polyimide. In another embodiment, the enlarged distal portion 309 of the device which covers the implant 100 is capable of transmitting light in the visible spectrum. This allows the orientation of the implant 100 to be visualized within the catheter 300. The distal end 304 may have a radiopaque marker (not shown) to locate the catheter 300 under fluoroscopy.

Figure 8:
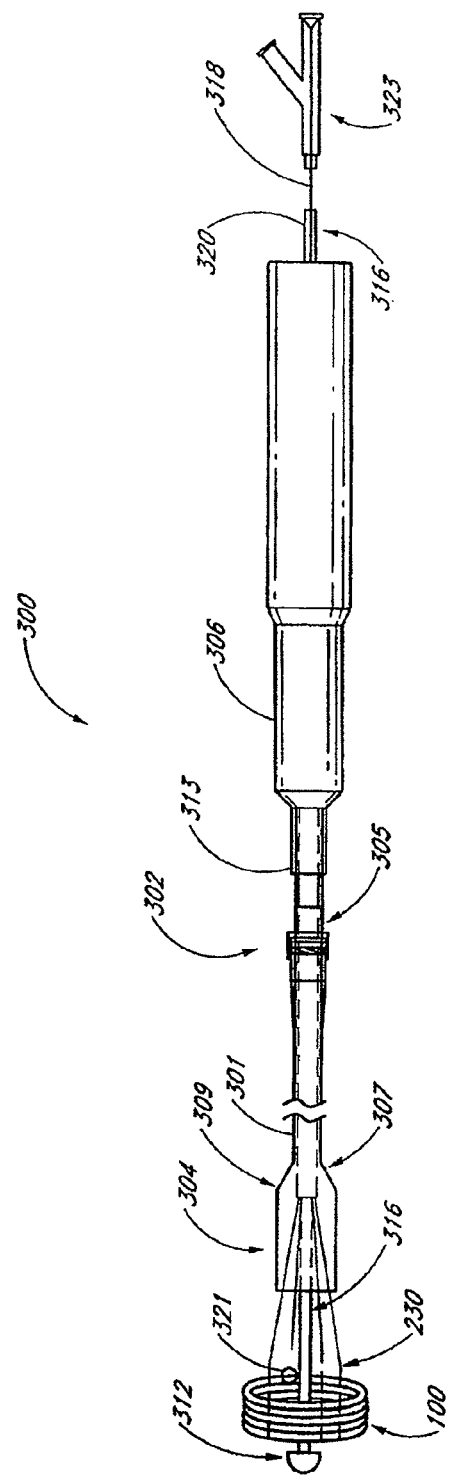
FIG. 8 is a side view of the deployment catheter of FIG. 7 with an outer sheath partially withdrawn and the implant deployed.
Figure 8A:
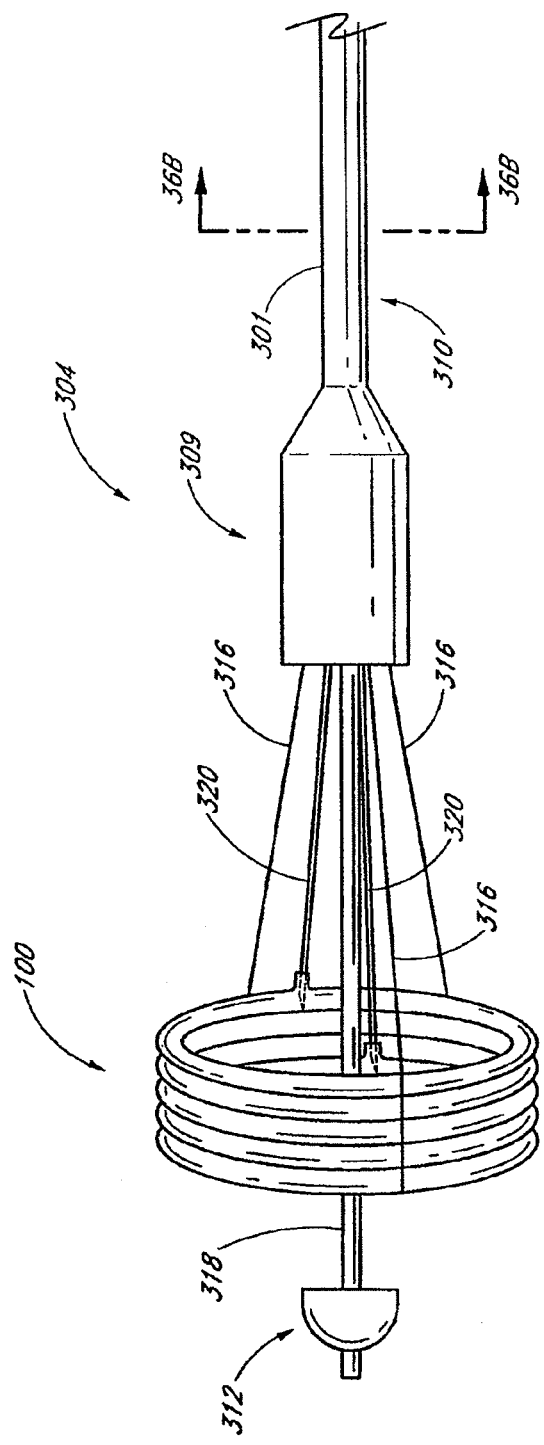
FIG. 8A is an enlarged view of the distal portion of the deployment catheter shown in FIG. 8.
Figure 9:
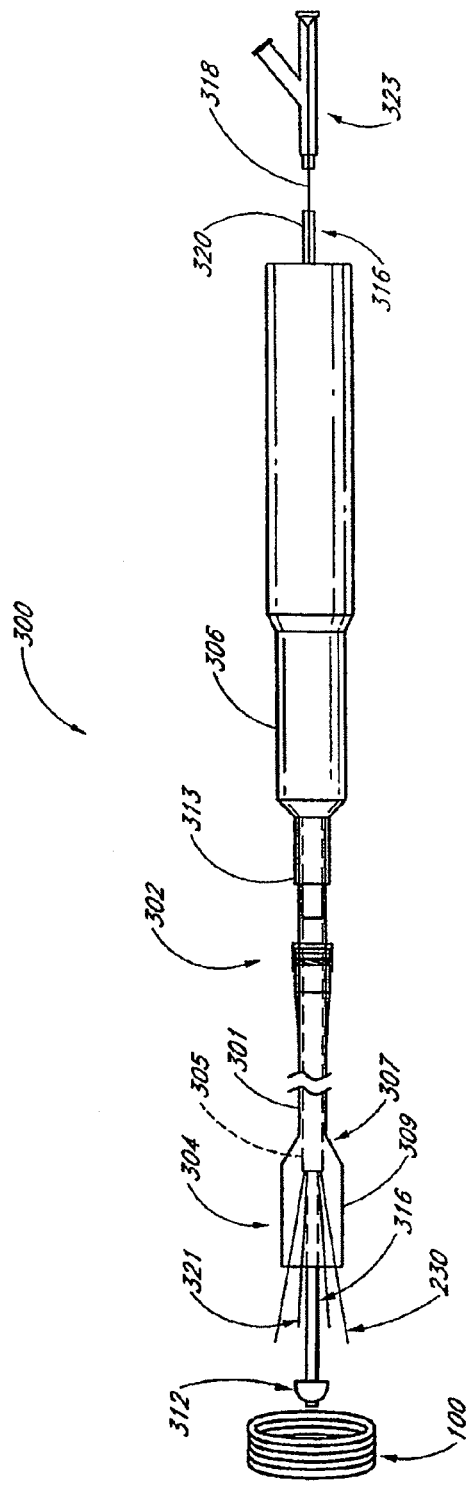
FIG. 9 is a side view of the deployment catheter of FIG. 7 with an outer sheath partially withdrawn and the implant deployed and detached.

With continued reference to FIGS. 6-9 and in particular FIGS. 8A and 8B, multiple tubes extend through the inner member 305. Specifically, in illustrated embodiment, a guidewire tube 318, two inflation tubes 320 and three control wire tubes 316 extend from the proximal end 303 to the distal end 307 of the inner member 307. Of course, in modified embodiments, various other numbers and combinations of tubes 316, 318, 320 can be used depending upon the configuration of the implant 100 and the deployment procedure. These tubes may be extruded from materials such as polyethene, polypropylene, nylon, PEEK, polyimid or other accepted polymer materials. They may also combine metallic elements such as coils or braids for additional support or be made from metallic tubings such as Nitinol or stainless steel. As will be explained below, the guidewire tube 318 is configured to receive a guidewire. The inflation tubes 320 are configured to delivery inflation media to the implant 100 and the control wire tubes 316 receive the control wires 230, which are coupled to the implant 100. As will be explained in more detail below, the inflation tubes 320 can include inner and outer members 320a, 320b (see FIG. 8B) for providing an inflation disconnect mechanism.

The inner member 305 material may also consist of stiffening members for transition zones or bump extrusions to reduced diameter and maintain correct pushability. Conventional guidewire passage through the catheter such as "over-the-wire" may be used or technology such as "rapid-exchange" may aid in procedure ease and catheter exchanges. Since multiple devices may be placed in a single catheterization, rapid-exchange may be preferred but not essential. Other features that may aid in ease of use include a slippery coating on the outer and or inner diameter such as mineral oil, MDX (silicone) or a hydrophilic layer to allow easy access to tortuous anatomy, or easier more controlled motion of one portion of the catheter relative to another portion of the catheter. It may be necessary or desirable to utilize a balloon to initiate radial contact of the device to its final position and location. In one embodiment, an inflation lumen and balloon placed distal to the hub is used. This balloon is used to pre-dilate the native valve annulus, vessel or ostium where the valve may be implanted. Elements to transmit signals externally could be imbedded into the catheter 300 for pressure and flow readings or Doppler information. These may include electro-mechanical sensors, such as piezo-electric devices, electrical sensors, wires, pressure portal or lumens or optical fibers.

As mentioned above, delivery of the implant 100 via catheterization of the implantation site can include a mechanism to deploy or expel the implant 100 into the vessel. This mechanism may include a push or pull member to transmit forces to the distal portion of the catheter 300. These forces may be applied externally to the body and utilize a handle at the proximal end of the catheter. Devices to transmit forces to the distal end may also include a rotational member to loosen or tighten, convert a torque into a translational force such as a threaded screw and nut or to add or subtract stiffness to the catheter or device, or to cause the device to assume a specific shape. The handle mechanism may also include a port for hydraulic pressures to be transmitted to the distal portion of the catheter or have the ability to generate hydraulic forces directly with the handle. These forces may include a pushing or pulling transmitted to the device or catheter, an exposure of the device to allow for implantation or to expel the device from the catheter. Further forces may include a radial or longitudinal expansion of the device or catheter to implant or size the location of implantation. The handle may also include connections to electrical signals to monitor information such as pressures, flow rates, temperature and Doppler information.

With reference to FIGS. 6 and 8, in the illustrated embodiment, the implant 100 is loaded between the distal portion 309 of the outer sheath 301 and the inner sheath 305. The distal portion 309 therefore forms a receptacle for the implant 100. A distal tip 312 can be coupled to the guidewire tube 318. The tip 312 can be used to close the receptacle when the catheter 300 is being advanced. The tip 312 can be distanced from the outer sheath 301 by proximally retracting the outer sheath 301, while holding the guidewire tube 318 stationary. Alternatively, the guidewire tube 318 can be advanced while holding the outer sheath 301 stationary. Control wires 230, which extend through the control wire tubes 316, can be coupled to implant 100 as described below and used to hold the implant 100 stationary as the implant outer sheath 301 is retracted. Alternatively the outer sheath 301 can be retracted with respect to the inner sheath 305, which acts as a pusher to push the implant 110 outer of the distal portion 309 of the outer sheath. The inflation channels 120 of the implant 100 are preferably connected to the inflation tubes 318 of the catheter by an inflation connection members 321.

With continued reference to FIG. 8, the inflation tubes 318, guidewire tube 320 and control wire tube 316 preferably extend to the proximal end 303 of the inner member 305. A connection hub 323 can be provided for connecting an inflation fluid source to the inflation tube 318. Various control mechanism (not shown) and sealing devices can also be provided for connecting to the control wires 230 and control wire tubes 316.

The control wires 230 and/or inflation lumen 318 can form part of a deployment mechanism for the implant 100. As the implant is navigated to the site, attachment between the implant 100 and catheter 300 is important. Many detachment mechanisms have been used to deploy devices such as stents and embolic coils through balloon expansion and simple pushable coils expelled from the distal end of a catheter. The implant 100 can utilize many different methods to implant 100 at the selected site such as an expulsion out the end of the catheter, a mechanical release mechanism such as a pin joint, unscrewing the device from the catheter delivery system, a tethered link such as a thread or wire, a fusible link as used in a GDC coil deployment, a cutting tool to sever a attachment of the device from the catheter, a threaded knot to tether the catheter to the device where the as the knot could be untied or cut, a hydraulic mechanism to deploy, expand or fracture a link between the catheter and the device. All above mentioned concepts can be enhanced by the utilization of the flexible tip 312 to allow acute articulation of the device and delivery catheter 300 to gain access to the implantation site.

After the implant 100 has been temporarily deployed or positioned, it may be advantageous to recapture or reposition the implant for optimal results. This may include a rotation or translation of the implant 100 or a complete removal and exchange for a different diameter, length or style device. Capture of an implanted device may require a second catheter to reengage the device to remove or reposition to a proper location. This catheter may be constructed from polymer tubing as described above including coils, braids, etc. Additionally there may be a braided section at the distal most potion of the catheter to accept or capture the device for retrieval from the body.

As mentioned above, the guidewire tube 320 preferably extends through the inner sheath 305 and the tip 312. The guidewire tube 320 may have an inside diameter of 0.035 to 0.042 in so that the device is compatible with common 0.035 or 0.038 guide wires. A modified embodiment includes a lumen 0.014 to 0.017 inches in diameter for compatibility with 0.014 in diameter guide wires. In a third embodiment, the guidewire lumen 320 is 0.039 to 0.080 in diameter, so that the device may be delivered over a larger than standard guide wire, or a diagnostic catheter, such as a pig tail catheter. This provides the advantage of a stiffer support to facilitate easier delivery through calcified valves. If a diagnostic catheter is used as a guidewire it may also serve as a port for contrast injection.

The guidewire tube 320 can be made from a lubricious material such as Teflon, polypropolene or a polymer impregnated with Teflon. It may also be coated with a lubricious or hydrophilic coating. The tube 320 can be constructed of multiple layers of material, including a lubricious inner layer and an outer layer to facilitate bonding to other catheter components.

The catheter 300 may be delivered over a guide wire to aid in positioning. The guide wire may pass coaxially through the entire length of the catheter or in modified embodiments may pass coaxially though only a portion of the catheter in a configuration known as rapid exchange. This allows shorter guide wires to be used if devices are to be exchanged out.

In the illustrated embodiment, the catheter 300 comprises the outer catheter shaft 301 and the inner catheter shaft 305 which move relative to one another. In order to minimize the risk of guidewire damage in a rapid exchange design where the catheter must pass through the wall of two sheaths which move relative to one another, a slot feature is desirable. Either the inner or outer elongate tube may contain a longitudinal slot in the area where the guide wire passes from the inner diameter to the outer diameter of the catheter assembly. The other elongate tube preferably contains a hollow pin to engage the slot and prevent the excessive movement of the two elongate members. The guide wire passes through the opening in the hollow pin. The inner diameter of the hollow pin is preferably oriented at an acute angle to the central axis of the catheter.

Another design to enable rapid exchange like performance is for the guide wire to enter the catheter tip through a side hole distal to the location of the prosthetic valve. The guidewire exits the tip of the system near the center of the catheter tip. This design enables the catheter to follow the guide wire across the native valve, while still allowing multiple devices to be exchanged easily on a short length guide wire.

As described above, the internal lumens of the catheter 300 can include the deployment control wires lumens 316, the inflation lumens 320, and an inner sheath 307 that encapsulates these lumens 316, 320. See e.g., FIG. 8B.

In one embodiment contrast media is passed through a lumen (e.g., the guidewire tube 320) of the device, and the lumen passes through the prosthetic valve 100. This allows visual evaluation of valve function by angiography, without crossing the valve with an additional device. In the preferred embodiment the lumen crosses the valve while the valve is in the catheter. In the preferred embodiment the lumen also serves as the guidewire tube 320, where the device is delivered over a guide wire. The wire may be removed from the lumen to allow more cross sectional area for contrast injection. The proximal end of the lumen near the handle of the device attaches to a fitting to allow the injection of contrast media with a power injector tool. The inner diameter of the lumen may range from 0.014 to 0.100 inch. The diameter of the lumen may vary along the length of the catheter, for example, Preferably the portion of the lumen which passes through the prosthetic valve is of a minimum possible diameter to allow both sufficient flow and the use of an adequate sized guidewire. This portion is preferably in the range of diameters from 0.014 to 0.080. The portion of the lumen extending along the length of the catheter proximal to the implant may be of larger diameter, the larger diameter allows flow of contrast media at lower pressure gradients, and the corresponding larger outside diameter does not increase the profile of the complete device. This portion of the lumen is preferably in the inside diameter range of 0.035 to 0.100 in. The distal portion of the lumen may contain a diffuser or transition to a larger diameter to minimize the pressure required to inject a sufficient volume of contrast media through the lumen. Multiple exit ports positioned around a nose cone also facilitate the flow of contrast media.

Access for the catheter 300 may be gained through a major artery such as the femoral artery. This access site is particularly appropriate for aortic valve replacement. Alternative access methods may be better suited for other valves. For example the tricuspid valve and possibly the pulmonary valve could best be accessed through the venous system. In this case, access would be gained through either a femoral vein or a jugular vein. The catheter would then be passed into the right atrium through the superior or inferior vena cava. Some embodiment of the current invention utilize a relatively large diameter catheter, which may not be compatable with the diameter of all patients femoral arteries. In these patients it may be desirable to access the common iliac artery or to use a transeptal approach and access the heart through the venous system.

As mentioned above, the catheter 300 includes an atraumatic tip 312 (see FIG. 4) to allow the device to be easily placed through the hemostasis valve of the introducer, and to easily cross the calcified aortic valve. The tip 312 may be cone shaped bullet shaped or hemispherical on the front end. The largest diameter of the tip 312 is preferably approximately the same as the distal portion 309 of the outer sheath 301. The tip 312 preferably steps down to a diameter slightly smaller than the inside diameter of the distal portion 309 of the outer sheath 301, so that the tip can engage the outer sheath 301 and provide a smooth transition. In the illustrated embodiment, the tip 312 is connected to the guide wire tube 320, and the guide wire lumen passes through a portion of the tip 312. The proximal side of the tip 312 also has a cone, bullet or hemispherical shape, so that the tip can easily be retraced back across the deployed valve 100, and into the deployment catheter 300. The tip 312 can be manufactured from a rigid polymer such as polycarbonate, or from a lower durometer material that allows flexibility, such as silicone. Alternatively, the tip 312 may be made from multiple materials with different durometers. For example, the portion of the tip 312 that engages the distal portion 309 of the outer sheath 301 can be manufactured from a rigid material, while the distal and or proximal ends of the tip are manufactured from a lower durometer material.

Figure 7:
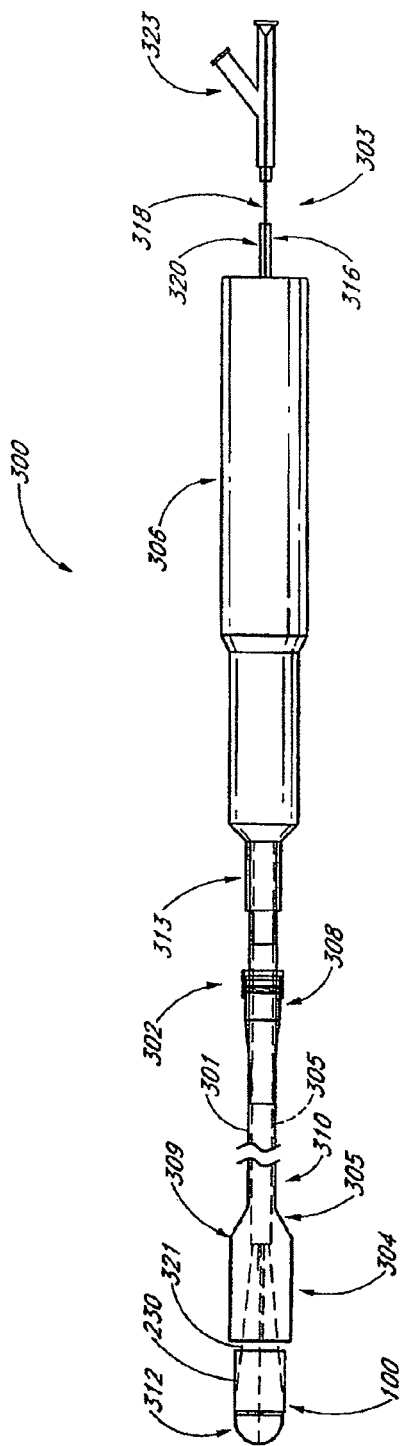
FIG. 7 is a side view of the deployment catheter of FIG. 6 with an outer sheath partially withdrawn.
Figure 7A:
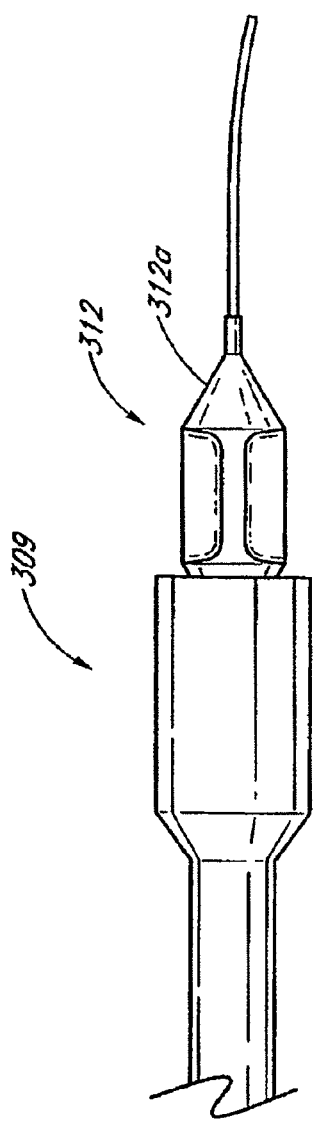
FIGS. 7A and 7B are side views of a modified embodiment of the distal end of the deployment catheter of FIG. 7.
Figure 7B:
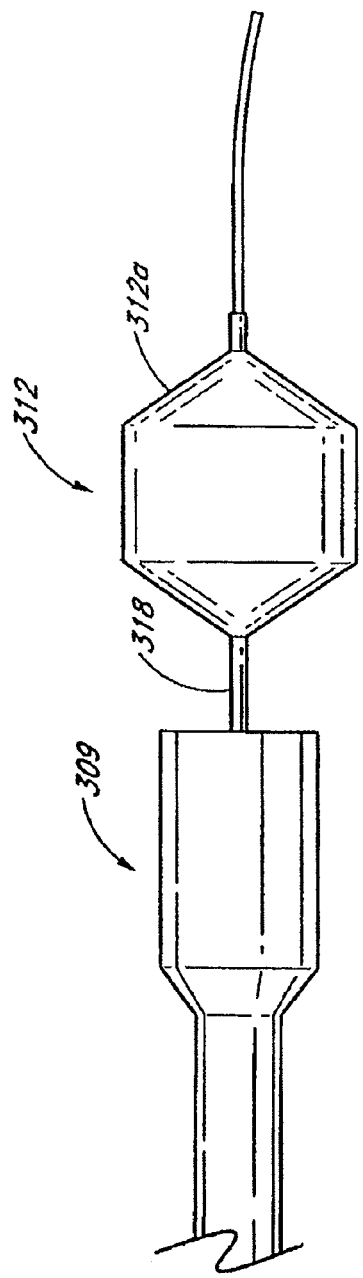

With reference to FIGS. 7A and 7B, in a modified embodiment, the area where the tip 312 of the device is located to house a balloon 312a for dilatation. This balloon 312a could use the lumen where a guidewire passes through (as shown in the illustrated embodiment) or a separate lumen for inflation and deflation. Since the distal portion 309 is rather large (10-24 French) it can be advantageous place to locate a large diameter balloon that could be used to pre or post dilate the valve area. There may also be a stent or other structure mounted to this balloon 312a for device securement or anchor deployment. The balloon 312a could also be covered with a thin membrane material similar to the "SOX" device commercialized by Boston Scientific and seen in U.S. Pat. No. 6,280,412 Pederson Jr. et al. This covering would allow the device to be hidden during delivery and could be exposed when inflated. In another embodiment, a tear-away sheath that covered the balloon 312a for protection can be used.

With reference back to FIG. 6, the hemostasis valve 308 is preferably is attached to the proximal end of the outer sheath 301 to prevent blood from leaking past the inner and outer sheaths 301, 305. In one embodiment, the valve 308 is a touhy-borscht design valve, or similar valve where the radial compression is easily adjustable. By adjusting the valve it is possible to lock the outer sheath 301 to the inner sheath 305 of the catheter 300 to prevent their accidental relative motion during delivery of the implant. At the proximal end 304 of the catheter 300, an additional hemostasis valve (not shown) is preferably provided to provide a seal for the multiple inflation lumens, and deployment control wires that must pass through the inner sheath 305. An additional port (not shown) can also be provided to allow the catheter 300 to be flushed to remove any trapped air before the catheter 300 is inserted into the patient.

Additional embodiments of delivery catheter and valve are described in a co-pending application titled "co-pending U.S. patent application titled "Low Crossing Profile Delivery Catheter for Cardiovascular Prosthetic Implant," filed on the same date as this application, U.S. Provisional No. 61/346,390 filed May 19, 2010 and U.S. Provisional No. 61/411,862 filed Nov. 9, 2010, the entireties of these applications are hereby incorporated by reference herein.

Valve Delivery

With reference to FIGS. 10A-C, in one embodiment, the implant 100 is initially deployed partially in the ventricle 32 (FIG. 10A) and then later pulled back into position at or near the native valve 34 annulus (FIG. 10B). Preferably, the valve 100 itself is placed just above the native valve annulus in the aortic root. The implant 100 can then be fully deployed (e.g., inflated) such that extends across the native valve annulus extending slightly to either side. See FIG. 10C. The deployment control wires 230 provide a mechanism for force transmission between the handle of the deployment catheter 300 and the implant 100. By moving all of the deployment control wires 230 together the device can be advanced or retracted in a proximal or distal direction. By advancing only a portion of the deployment control wires 230 relative to the other deployment control wires 230, the angle or orientation of the wires can be adjusted relative to the native anatomy. Radiopaque markers on the implant 100 or on the deployment control wires 230 or the radio-opacity of the wires 230 themselves, help to indicate the orientation of the implant 100 as the operator positions and orients the implant 100.

Other Applications

The inflation media describe herein can be used in various implantable devices. For example, the inflation media can be used to inflate various types of inflatable vascular grafts, inflatable stents, etc. In some embodiments, the inflation media may be used in orthopedic application, such as inflatable bone fixation devices and other orthopedic implants. The disclosed inflation media is particularly suitable for inflating implantable devices through a small catheter due to its low initial viscosity. For example, the inflation media can be used with an 18 French catheter and implants as described in the co-pending U.S. patent application titled "Low Crossing Profile Delivery Catheter for Cardiovascular Prosthetic Implant," filed on the same date of this application. The disclosure of this co-pending application is incorporated in its entirety herein by reference. The inflation media is also soluble enough in aqueous solution or blood to minimize the risk of embolism in case of a leak during delivery of the inflation media and the inflation process. At the same time, it offers superior strength and creep resistance for maintaining the structural integrity of various implants when solidified.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments disclosed herein. Similarly, the various features and steps discussed above, as well as other known equivalents for each such feature or step, can be mixed and matched by one of ordinary skill in this art to perform methods in accordance with principles described herein. Additionally, the methods which is described and illustrated herein is not limited to the exact sequence of acts described, nor is it necessarily limited to the practice of all of the acts set forth. Other sequences of events or acts, or less than all of the events, or simultaneous occurrence of the events, may be utilized in practicing the embodiments of the invention.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein.

What is claimed is:

1. An inflation media comprising:
an epoxy resin comprising a first compound having at least one N,N-bis(oxiran-2-ylmethyl)aniline segment and a second compound having at least two oxirane groups on a backbone of no more than five carbons;
a hardener comprising at least one cycloaliphatic amine; and
wherein a mixture of the epoxy resin and the hardener has an average viscosity of less than about 100 cps at about 37° C. over the first 10 minutes of formation; and
wherein the first compound is about 40% to about 60% by weight and the second compound is about 40% to about 60% by weight of the epoxy resin.

2. The inflation media of claim 1, wherein the first compound is N,N-diglycidyl-4-glycidyloxyaniline or 4,4'-methylenebis(N,N-diglycidylaniline).

3. The inflation media of claim 1, wherein the second compound is selected from the group consisting of 1,4-butanediol diglycidyl ether, 1,2-ethanediol diglycidyl ether, polyglycidyl ether, and 1,3-butadiene diepoxide.

4. The inflation media of claim 1, wherein the at least one cycloaliphatic amine is selected from the group consisting of isophorone diamine, 1,3-bis-aminocyclohexane, diamino cyclohexane, n-aminoethylpiperazine, and n-aminopropylpiperazine.

5. The inflation media of claim 1, wherein the hardener comprises isophorone diamine and 1,3-bis-aminocyclohexane.

6. The inflation media of claim 1, wherein the first compound is N,N-diglycidyl-4-glycidyloxyaniline, the second compound is 1,4-butanediol diglycidyl ether, and the hardener comprises isophorone diamine and 1,3-bis-aminocyclohexane.

7. The inflation media of claim 1, wherein the epoxy resin further comprises a third compound having at least one of the following group:

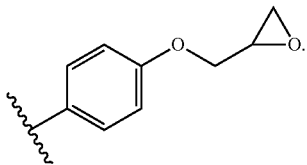 [SMILES: *c1ccc(OCC2CO2)cc1]

8. The inflation media of claim 7, wherein the third compound is selected from the group consisting of tris(4-hydroxyphenyl)methane triglycidyl ether, bisphenol-A diglycidyl ether, bisphenol-F diglycidyl ether and resorcinol diglycidyl ether.

9. The inflation media of claim 1, wherein the hardener further comprises an aliphatic amine selected from the group consisting of diethylene triamine, tri-ethylene tetraamine and tetraethylenepentamine.

10. The inflation media of claim 9, wherein the cycloaliphatic amine is about 75% to about 100% and the aliphatic amine is about 0% to about 25% by weight of the hardener.

11. The inflation media of claim 1, wherein the hardener further comprises a radio-opaque compound.

12. The inflation media of claim 11, wherein the radio-opaque compound is selected from the group consisting of 3,5-diiodosalicylic acid, 3-iodo-1-propanol, 2,3,5-triiodobenzoic acid, 3,5-diiodobenzoic acid, 4-iodophenol, 2,4,6-triiodophenol, iodo benzoic acid, iodo salicylic acid, iodobenzene and diiodobenzene.

13. The inflation media of claim 1, wherein the hardener further comprises a catalyst.

14. The inflation media of claim 13, where in the catalyst is water, polybenzoic acid or polyphenol.

* * * * *